US010118026B2

(12) United States Patent
Grubac et al.

(10) Patent No.: US 10,118,026 B2
(45) Date of Patent: *Nov. 6, 2018

(54) IMPLANTABLE MEDICAL DEVICE FIXATION

(71) Applicant: Medtronic, Inc., Minneopolis, MN (US)

(72) Inventors: Vladimir Grubac, Brooklyn Park, MN (US); Matthew D. Bonner, Plymouth, MN (US); Raymond W. Usher, Ham Lake, MN (US); Thomas A. Anderson, New Hope, MN (US); Arshad A. Alfoqaha, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/809,579

(22) Filed: Nov. 10, 2017

(65) Prior Publication Data

US 2018/0064927 A1   Mar. 8, 2018

Related U.S. Application Data

(63) Continuation of application No. 14/193,306, filed on Feb. 28, 2014, now Pat. No. 9,844,659, which is a
(Continued)

(51) Int. Cl.
*A61N 1/05*     (2006.01)
*A61N 1/375*    (2006.01)

(52) U.S. Cl.
CPC .............. *A61N 1/05* (2013.01); *A61N 1/0573* (2013.01); *A61N 1/3756* (2013.01); *A61N 1/37518* (2017.08)

(58) Field of Classification Search
CPC ........ A61N 1/05; A61N 1/0573; A61N 1/059; A61N 1/3756
(Continued)

(56) References Cited

U.S. PATENT DOCUMENTS 2,108,206 A   2/1938 Meeker
3,754,555 A   8/1973 Schmitt
(Continued)

FOREIGN PATENT DOCUMENTS

CN   1882370       12/2006
EP   0004967 A2   10/1997
(Continued)

OTHER PUBLICATIONS

Medtronic, Inc., "Cardiac Resynchronization Therapy for Heart Failure Management—Implant and Follow-up—Brief Overview" 4 pages (2002).
(Continued)

*Primary Examiner* — Christopher A Flory

(57) ABSTRACT

Various fixation techniques for implantable medical device (IMDs) are described. In one example, an assembly comprises an IMD; and a set of active fixation tines attached to the IMD. The active fixation tines in the set are deployable from a spring-loaded position in which distal ends of the active fixation tines point away from the IMD to a hooked position in which the active fixation tines bend back towards the IMD. The active fixation tines are configured to secure the IMD to a patient tissue when deployed while the distal ends of the active fixation tines are positioned adjacent to the patient tissue.

29 Claims, 10 Drawing Sheets

Related U.S. Application Data continuation of application No. 13/096,881, filed on Apr. 28, 2011, now Pat. No. 9,775,982.

(60) Provisional application No. 61/428,067, filed on Dec. 29, 2010.

(58) Field of Classification Search
USPC .......... 607/36, 119, 126, 127; 600/373, 375
See application file for complete search history.

(56) References Cited

U.S. PATENT DOCUMENTS

| | | |
|---|---|---|
| 3,814,104 A | 6/1974 | Irnich et al. |
| 3,835,864 A | 9/1974 | Rasor et al. |
| 3,943,936 A | 3/1976 | Rasor et al. |
| 3,976,082 A | 8/1976 | Schmitt |
| 3,978,865 A | 9/1976 | Trabucco |
| 4,011,875 A | 3/1977 | Lehr et al. |
| 4,035,909 A | 7/1977 | Dey |
| 4,103,690 A | 8/1978 | Harris |
| 4,112,952 A | 9/1978 | Thomas et al. |
| 4,144,890 A | 3/1979 | Hess |
| 4,177,818 A | 12/1979 | De Pedro |
| 4,269,198 A | 5/1981 | Stokes |
| 4,280,512 A | 7/1981 | Karr et al. |
| 4,376,811 A | 3/1983 | Goebel |
| 4,378,023 A | 3/1983 | Trabucco |
| 4,465,079 A | 8/1984 | Dickhudt |
| 4,494,531 A | 1/1985 | Gianturco |
| 4,519,404 A | 5/1985 | Fleischhacker |
| 4,590,949 A | 5/1986 | Pohndorf |
| 4,641,664 A | 2/1987 | Botvidsson |
| 4,727,873 A | 3/1988 | Mobin-Uddin |
| 4,731,305 A | 3/1988 | Goebel et al. |
| 4,858,623 A | 8/1989 | Bradshaw et al. |
| 5,002,067 A | 3/1991 | Berthelsen et al. |
| 5,024,239 A | 6/1991 | Rosenstein |
| 5,098,393 A | 3/1992 | Amplatz et al. |
| 5,179,962 A | 1/1993 | Dutcher et al. |
| 5,221,269 A | 6/1993 | Miller et al. |
| 5,237,996 A | 8/1993 | Waldman et al. |
| 5,249,574 A | 10/1993 | Bush et al. |
| 5,255,679 A | 10/1993 | Imran |
| 5,258,678 A | 11/1993 | Futami |
| 5,265,608 A | 11/1993 | Lee et al. |
| 5,282,845 A | 2/1994 | Bush et al. |
| 5,306,581 A | 4/1994 | Taylor et al. |
| 5,314,462 A | 5/1994 | Heil, Jr. et al. |
| 5,324,316 A | 6/1994 | Schulman et al. |
| 5,324,327 A | 6/1994 | Cohen |
| 5,330,525 A | 7/1994 | Proctor |
| 5,358,514 A | 10/1994 | Schulman et al. |
| 5,368,601 A | 11/1994 | Sauer et al. |
| 5,383,922 A | 1/1995 | Zipes et al. |
| 5,387,233 A | 2/1995 | Alferness et al. |
| 5,411,535 A | 5/1995 | Fujii et al. |
| 5,466,255 A | 11/1995 | Franchi |
| 5,492,119 A | 2/1996 | Abrams |
| 5,507,757 A | 4/1996 | Sauer et al. |
| 5,507,802 A | 4/1996 | Imran |
| 5,514,174 A | 5/1996 | Heil, Jr. et al. |
| 5,540,734 A | 7/1996 | Zabara |
| 5,545,207 A | 8/1996 | Smits et al. |
| 5,545,219 A | 8/1996 | Kuzma |
| 5,562,723 A | 10/1996 | Rugland et al. |
| 5,766,234 A | 6/1998 | Chen et al. |
| 5,776,632 A | 7/1998 | Honegger |
| 5,814,089 A | 9/1998 | Stokes et al. |
| 5,824,041 A | 10/1998 | Lenker et al. |
| 5,840,076 A | 11/1998 | Swanson et al. |
| 5,860,974 A | 1/1999 | Abele |
| 5,871,532 A | 2/1999 | Schroeppel |
| 5,885,258 A | 3/1999 | Sachdeva et al. |
| 5,895,391 A | 4/1999 | Farnholtz |
| 5,897,584 A | 4/1999 | Herman |
| 5,964,754 A | 10/1999 | Osypka |
| 5,968,052 A | 10/1999 | Sullivan, III et al. |
| 5,984,944 A | 11/1999 | Forber |
| 6,010,476 A | 1/2000 | Saadat |
| 6,024,752 A | 2/2000 | Horn et al. |
| 6,074,401 A | 6/2000 | Gardiner et al. |
| 6,113,593 A | 9/2000 | Tu et al. |
| 6,120,480 A | 9/2000 | Zhang et al. |
| 6,136,005 A | 10/2000 | Goode et al. |
| 6,149,658 A | 11/2000 | Gardiner et al. |
| 6,183,305 B1 | 2/2001 | Doan et al. |
| 6,238,813 B1 | 5/2001 | Maile et al. |
| 6,258,098 B1 | 7/2001 | Taylor et al. |
| 6,266,568 B1 | 7/2001 | Mann et al. |
| 6,270,489 B1 | 8/2001 | Wise et al. |
| 6,308,105 B1 | 10/2001 | Duysens et al. |
| 6,322,586 B1 | 11/2001 | Monroe et al. |
| 6,350,278 B1 | 2/2002 | Lenker et al. |
| 6,352,561 B1 | 3/2002 | Leopold et al. |
| 6,395,017 B1 | 5/2002 | Dwyer et al. |
| 6,409,674 B1 | 6/2002 | Brockway et al. |
| 6,434,431 B1 | 8/2002 | Camps et al. |
| 6,468,301 B1 | 10/2002 | Amplatz et al. |
| 6,477,423 B1 | 11/2002 | Jenkins |
| 6,498,951 B1 | 12/2002 | Larson et al. |
| 6,505,075 B1 | 1/2003 | Weiner |
| 6,510,332 B1 | 1/2003 | Greenstein |
| 6,514,265 B2 | 2/2003 | Ho et al. |
| 6,514,280 B1 | 2/2003 | Gilson |
| 6,516,230 B2 | 2/2003 | Williams et al. |
| 6,529,777 B1 | 3/2003 | Holmström et al. |
| 6,551,332 B1 | 4/2003 | Nguyen et al. |
| 6,582,400 B1 | 6/2003 | Hawk et al. |
| 6,585,634 B1 | 7/2003 | Henckel et al. |
| 6,589,238 B2 | 7/2003 | Edwards et al. |
| 6,600,955 B1 | 7/2003 | Zierhofer |
| 6,607,541 B1 | 8/2003 | Gardiner et al. |
| 6,607,843 B2 | 8/2003 | Ruth, II et al. |
| 6,613,059 B2 | 9/2003 | Schaller et al. |
| 6,623,518 B2 | 9/2003 | Thompson et al. |
| 6,626,899 B2 | 9/2003 | Houser et al. |
| 6,626,916 B1 | 9/2003 | Yeung et al. |
| 6,641,593 B1 | 11/2003 | Schaller et al. |
| 6,645,143 B2 | 11/2003 | VanTassel et al. |
| 6,679,902 B1 | 1/2004 | Boyle et al. |
| 6,684,109 B1 | 1/2004 | Osypka |
| 6,689,056 B1 | 2/2004 | Kilcoyne et al. |
| 6,695,859 B1 | 2/2004 | Golden et al. |
| 6,697,677 B2 | 2/2004 | Dahl et al. |
| 6,746,404 B2 | 6/2004 | Schwartz |
| 6,783,499 B2 | 8/2004 | Schwartz |
| 6,840,956 B1 | 1/2005 | Wolinsky et al. |
| 6,842,648 B2 | 1/2005 | Partridge et al. |
| 6,866,650 B2 | 3/2005 | Stevens et al. |
| 6,876,885 B2 | 4/2005 | Swoyer et al. |
| 6,889,093 B1 | 5/2005 | Flammang |
| 6,895,283 B2 | 5/2005 | Erickson et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,932,837 B2 | 8/2005 | Amplatz et al. |
| 6,960,221 B2 | 11/2005 | Ho et al. |
| 7,047,084 B2 | 5/2006 | Erickson et al. |
| 7,054,692 B1 | 5/2006 | Whitehurst et al. |
| 7,056,286 B2 | 6/2006 | Ravenscroft et al. |
| 7,060,038 B2 | 6/2006 | Letort et al. |
| 7,070,881 B2 | 7/2006 | Kishiyama et al. |
| 7,072,703 B2 | 7/2006 | Zhang et al. |
| 7,099,718 B1 | 8/2006 | Thacker et al. |
| 7,128,765 B2 | 10/2006 | Paulot et al. |
| 7,147,604 B1 | 12/2006 | Allen et al. |
| 7,172,620 B2 | 2/2007 | Gilson |
| 7,177,702 B2 | 2/2007 | Wallace et al. |
| 7,181,288 B1 | 2/2007 | Rezai et al. |
| 7,191,015 B2 | 3/2007 | Lamson et al. |
| 7,236,821 B2 | 6/2007 | Cates et al. |
| 7,288,096 B2 | 10/2007 | Chin |
| 7,291,186 B2 | 11/2007 | Zhang |

(56) References Cited

U.S. PATENT DOCUMENTS

| | | |
|---|---|---|
| 7,294,334 B1 | 11/2007 | Michal et al. |
| 7,309,349 B2 | 12/2007 | Jackson et al. |
| 7,364,541 B2 | 4/2008 | Chu et al. |
| 7,410,512 B2 | 8/2008 | Tsukamoto et al. |
| 7,473,266 B2 | 1/2009 | Glaser |
| 7,499,758 B2 | 3/2009 | Cates et al. |
| 7,572,228 B2 | 8/2009 | Wolinsky et al. |
| 7,647,109 B2 | 1/2010 | Hastings et al. |
| 7,650,186 B2 | 1/2010 | Hastings et al. |
| 7,699,059 B2 | 4/2010 | Fonseca et al. |
| 7,704,245 B2 | 4/2010 | Dittman et al. |
| 7,717,854 B2 | 5/2010 | Mann et al. |
| 7,740,655 B2 | 6/2010 | Birdsall |
| 7,765,014 B2 | 7/2010 | Eversull et al. |
| 7,769,420 B2 | 8/2010 | Silver et al. |
| 7,776,080 B2 | 8/2010 | Bei et al. |
| 7,783,338 B2 | 8/2010 | Ainsworth et al. |
| 7,785,360 B2 | 8/2010 | Freitag |
| 7,797,053 B2 | 9/2010 | Atkinson et al. |
| 7,801,626 B2 | 9/2010 | Moser |
| 7,871,430 B2 | 1/2011 | Pavcnik et al. |
| 7,890,186 B2 | 2/2011 | Wardle et al. |
| 7,938,840 B2 | 5/2011 | Golden et al. |
| 7,963,952 B2 | 6/2011 | Wright, Jr. et al. |
| 8,062,327 B2 | 11/2011 | Chanduszko et al. |
| 8,103,361 B2 | 1/2012 | Moser |
| 8,340,780 B2 | 12/2012 | Hastings et al. |
| 8,352,028 B2 | 1/2013 | Wenger |
| 8,409,090 B2 | 4/2013 | Smith et al. |
| 8,496,614 B2 | 7/2013 | Birk et al. |
| 8,715,332 B2 | 5/2014 | Tan et al. |
| 8,818,504 B2 | 8/2014 | Bodner et al. |
| 9,020,611 B2 * | 4/2015 | Khairkhahan ......... A61N 1/375 607/127 |
| 9,125,765 B2 | 9/2015 | Melsheimer |
| 9,220,906 B2 | 12/2015 | Griswold et al. |
| 9,227,040 B2 | 1/2016 | Rosenberg et al. |
| 9,242,102 B2 * | 1/2016 | Khairkhahan ..... A61N 1/37205 |
| 9,283,065 B2 | 3/2016 | Kleshinski et al. |
| 9,339,197 B2 | 5/2016 | Griswold et al. |
| 9,775,982 B2 * | 10/2017 | Grubac .................... A61N 1/05 |
| 9,833,625 B2 | 12/2017 | Waldhauser et al. |
| 9,844,659 B2 * | 12/2017 | Grubac ................... A61N 1/05 |
| 2001/0002300 A1 | 5/2001 | Tinker et al. |
| 2001/0047181 A1 | 11/2001 | Ho et al. |
| 2002/0010490 A1 | 1/2002 | Schaller et al. |
| 2002/0111659 A1 | 4/2002 | Davis et al. |
| 2002/0082610 A1 | 6/2002 | Cionata et al. |
| 2002/0103521 A1 | 8/2002 | Swoyer et al. |
| 2002/0120250 A1 | 8/2002 | Altman |
| 2002/0147485 A1 | 10/2002 | Mamo et al. |
| 2002/0156513 A1 | 10/2002 | Borkan |
| 2002/0198572 A1 | 12/2002 | Weiner |
| 2003/0004537 A1 | 1/2003 | Boyle et al. |
| 2003/0036790 A1 | 2/2003 | Corbett, III et al. |
| 2003/0045901 A1 | 3/2003 | Opolski |
| 2003/0069623 A1 | 4/2003 | Stypulkowski |
| 2003/0078603 A1 | 4/2003 | Schaller et al. |
| 2003/0088301 A1 | 5/2003 | King |
| 2003/0093118 A1 | 5/2003 | Ho et al. |
| 2003/0093130 A1 | 5/2003 | Stypulkowski |
| 2003/0120328 A1 | 6/2003 | Jenkins et al. |
| 2003/0125790 A1 | 7/2003 | Fastovsky et al. |
| 2003/0176907 A1 | 9/2003 | Tarvin |
| 2003/0199974 A1 | 10/2003 | Lee et al. |
| 2003/0236545 A1 | 12/2003 | Gilson |
| 2004/0015193 A1 | 1/2004 | Lamson et al. |
| 2004/0059393 A1 | 3/2004 | Policker et al. |
| 2004/0093053 A1 | 5/2004 | Gerber et al. |
| 2004/0101746 A1 | 5/2004 | Ota et al. |
| 2004/0102797 A1 | 5/2004 | Golden et al. |
| 2004/0111099 A1 | 6/2004 | Nguyen et al. |
| 2004/0111139 A1 | 6/2004 | McCreery |
| 2004/0116878 A1 | 6/2004 | Byrd et al. |
| 2004/0116992 A1 | 6/2004 | Wardle et al. |
| 2004/0147973 A1 | 7/2004 | Hauser |
| 2004/0148007 A1 | 7/2004 | Jackson et al. |
| 2004/0133229 A1 | 9/2004 | Starkebaum et al. |
| 2004/0176782 A1 | 9/2004 | Hanse et al. |
| 2004/0181206 A1 | 9/2004 | Chiu et al. |
| 2004/0185337 A1 | 9/2004 | Ishizaki |
| 2004/0193092 A1 | 9/2004 | Deal |
| 2004/0215230 A1 | 10/2004 | Frazier et al. |
| 2004/0230279 A1 | 11/2004 | Cates et al. |
| 2004/0243206 A1 | 12/2004 | Tadlock |
| 2004/0249433 A1 | 12/2004 | Freitag |
| 2004/0254572 A1 | 12/2004 | McIntyre et al. |
| 2005/0015129 A1 | 1/2005 | Mische |
| 2005/0021054 A1 | 1/2005 | Ainsworth et al. |
| 2005/0060014 A1 | 3/2005 | Swoyer et al. |
| 2005/0065601 A1 | 3/2005 | Lee et al. |
| 2005/0070924 A1 | 3/2005 | Schaller et al. |
| 2005/0080435 A1 | 4/2005 | Smith et al. |
| 2005/0090884 A1 | 4/2005 | Honeck |
| 2005/0096718 A1 | 5/2005 | Gerber et al. |
| 2005/0102006 A1 | 5/2005 | Whitehurst et al. |
| 2005/0107861 A1 | 5/2005 | Harris et al. |
| 2005/0107862 A1 | 5/2005 | Ohlenschlaeger |
| 2005/0149141 A1 | 7/2005 | Starkebaum |
| 2005/0149142 A1 | 7/2005 | Starkebaum |
| 2005/0154321 A1 | 7/2005 | Wolinksy et al. |
| 2005/0171479 A1 | 8/2005 | Hruska et al. |
| 2005/0209653 A1 | 9/2005 | Herbert et al. |
| 2005/0221054 A1 | 10/2005 | Kawano et al. |
| 2005/0222632 A1 | 10/2005 | Obino |
| 2005/0245840 A1 | 11/2005 | Christopherson et al. |
| 2005/0245986 A1 | 11/2005 | Starkebaum |
| 2005/0246004 A1 | 11/2005 | Cameron et al. |
| 2005/0267487 A1 | 12/2005 | Christensen et al. |
| 2005/0287859 A1 | 12/2005 | Komizo et al. |
| 2005/0288596 A1 | 12/2005 | Eigler et al. |
| 2006/0047205 A1 | 3/2006 | Ludomirsky et al. |
| 2006/0057458 A1 | 3/2006 | O'Dea et al. |
| 2006/0069422 A9 | 3/2006 | Bolduc et al. |
| 2006/0079943 A1 | 4/2006 | Narciso, Jr. |
| 2006/0079950 A1 | 4/2006 | Lehnhardt et al. |
| 2006/0084965 A1 | 4/2006 | Young |
| 2006/0085041 A1 | 4/2006 | Hastings et al. |
| 2006/0085042 A1 | 4/2006 | Hastings et al. |
| 2006/0085045 A1 | 4/2006 | Harel et al. |
| 2006/0085971 A1 | 4/2006 | Andrews et al. |
| 2006/0095078 A1 | 5/2006 | Tronnes |
| 2006/0099238 A1 | 5/2006 | Khosravi et al. |
| 2006/0100686 A1 | 5/2006 | Bolduc et al. |
| 2006/0149324 A1 | 7/2006 | Mann et al. |
| 2006/0149330 A1 | 7/2006 | Mann et al. |
| 2006/0206163 A1 | 9/2006 | Wahlstrand et al. |
| 2006/0206165 A1 | 9/2006 | Jaax et al. |
| 2006/0206166 A1 | 9/2006 | Weiner |
| 2006/0212096 A1 | 9/2006 | Stevenson |
| 2006/0222942 A1 | 10/2006 | Zhao et al. |
| 2006/0241705 A1 | 10/2006 | Neumann et al. |
| 2006/0241733 A1 | 10/2006 | Zhang et al. |
| 2006/0247753 A1 | 11/2006 | Wenger et al. |
| 2006/0259128 A1 | 11/2006 | Pavcnik et al. |
| 2006/0271137 A1 | 11/2006 | Stanton-Hicks |
| 2006/0275659 A1 | 12/2006 | Kim et al. |
| 2007/0027514 A1 | 2/2007 | Gerber |
| 2007/0027515 A1 | 2/2007 | Gerber |
| 2007/0043414 A1 | 2/2007 | Fifer et al. |
| 2007/0043424 A1 | 2/2007 | Pryor |
| 2007/0073391 A1 | 3/2007 | Bourang et al. |
| 2007/0088230 A1 | 4/2007 | Terashi et al. |
| 2007/0088396 A1 | 4/2007 | Jacobson |
| 2007/0088418 A1 | 4/2007 | Jacobson |
| 2007/0129637 A1 | 6/2007 | Wolinsky et al. |
| 2007/0135826 A1 | 6/2007 | Zaver et al. |
| 2007/0150020 A1 | 6/2007 | Hokanson et al. |
| 2007/0154801 A1 | 7/2007 | Hyung et al. |
| 2007/0156126 A1 | 7/2007 | Flaherty |
| 2007/0179552 A1 | 8/2007 | Dennis et al. |
| 2007/0197939 A1 | 8/2007 | Wallace et al. |
| 2007/0219590 A1 | 9/2007 | Hastings et al. |
| 2007/0247786 A1 | 10/2007 | Aamodt et al. |

(56) References Cited

U.S. PATENT DOCUMENTS

| | | |
|---|---|---|
| 2007/0255295 A1 | 11/2007 | Starkebaum et al. |
| 2007/0255383 A1 | 11/2007 | Gerber et al. |
| 2007/0274565 A1 | 11/2007 | Penner |
| 2007/0276461 A1 | 11/2007 | Andreas et al. |
| 2007/0293090 A1 | 12/2007 | Cowan et al. |
| 2007/0293909 A1 | 12/2007 | Cowan et al. |
| 2007/0293922 A1 | 12/2007 | Soltis et al. |
| 2007/0299492 A1 | 12/2007 | Zhang et al. |
| 2008/0009750 A1 | 1/2008 | Aeby et al. |
| 2008/0051704 A1 | 2/2008 | Patel et al. |
| 2008/0071178 A1 | 3/2008 | Greenland et al. |
| 2008/0077227 A1 | 3/2008 | Ouellette et al. |
| 2008/0103578 A1 | 5/2008 | Gerber |
| 2008/0125844 A1 | 5/2008 | Swoyer et al. |
| 2008/0132981 A1 | 6/2008 | Gerber |
| 2008/0132982 A1 | 6/2008 | Gerber |
| 2008/0148554 A1 | 6/2008 | Merrill et al. |
| 2008/0172118 A1 | 7/2008 | Johnson et al. |
| 2008/0255475 A1 | 10/2008 | Kondrosky et al. |
| 2008/0262422 A1 | 10/2008 | Cahill |
| 2008/0275350 A1 | 11/2008 | Liao et al. |
| 2008/0283066 A1 | 11/2008 | Delgado et al. |
| 2008/0300672 A1 | 12/2008 | Kassab et al. |
| 2009/0043367 A1 | 2/2009 | Zilberman et al. |
| 2009/0082828 A1* | 3/2009 | Ostroff .................. A61N 1/3756 607/36 |
| 2009/0082843 A1 | 3/2009 | Cox et al. |
| 2009/0099641 A1 | 4/2009 | Wu et al. |
| 2009/0105799 A1 | 4/2009 | Hekmat et al. |
| 2009/0131970 A1 | 5/2009 | Chanduszko et al. |
| 2009/0157092 A1 | 6/2009 | Blumenkranz et al. |
| 2009/0163969 A1 | 6/2009 | Donofrio |
| 2009/0192514 A1 | 6/2009 | Feinberg et al. |
| 2009/0177095 A1 | 7/2009 | Aeby et al. |
| 2009/0182412 A1 | 7/2009 | Tan et al. |
| 2009/0192585 A1 | 7/2009 | Bloom et al. |
| 2009/0192601 A1 | 7/2009 | Rafiee et al. |
| 2009/0234367 A1 | 9/2009 | Verma |
| 2009/0270741 A1 | 10/2009 | Vanney et al. |
| 2009/0275818 A1 | 11/2009 | Rau et al. |
| 2009/0299429 A1 | 12/2009 | Mayotte |
| 2009/0306539 A1 | 12/2009 | Woodruff et al. |
| 2009/0326346 A1 | 12/2009 | Kracker et al. |
| 2010/0004730 A1 | 1/2010 | Benjamin et al. |
| 2010/0030063 A1 | 2/2010 | Lee et al. |
| 2010/0030139 A1 | 2/2010 | Copa |
| 2010/0057009 A1 | 3/2010 | McQueen et al. |
| 2010/0063478 A1 | 3/2010 | Selkee |
| 2010/0076398 A1 | 3/2010 | Scheurer et al. |
| 2010/0082087 A1 | 4/2010 | Silipo et al. |
| 2010/0094400 A1 | 4/2010 | Bolduc et al. |
| 2010/0168612 A1 | 7/2010 | Ducharme et al. |
| 2010/0179561 A1 | 7/2010 | Pilarksi et al. |
| 2010/0185172 A1 | 7/2010 | Fabro |
| 2010/0234698 A1 | 9/2010 | Manstom et al. |
| 2010/0274221 A1 | 10/2010 | Sigg et al. |
| 2010/0274227 A1 | 10/2010 | Khairkhahan et al. |
| 2010/0274345 A1 | 10/2010 | Rust |
| 2010/0304209 A1 | 12/2010 | Lund et al. |
| 2010/0305653 A1 | 12/2010 | Lund et al. |
| 2011/0077708 A1 | 3/2011 | Ostroff |
| 2011/0160557 A1 | 6/2011 | Cinbis et al. |
| 2011/0190842 A1 | 8/2011 | Johnson et al. |
| 2011/0220274 A1 | 9/2011 | Erskine |
| 2011/0251662 A1* | 10/2011 | Griswold ........... A61N 1/37205 607/128 |
| 2011/0264194 A1 | 10/2011 | Griswold |
| 2011/0313503 A1 | 12/2011 | Berra et al. |
| 2012/0029598 A1 | 2/2012 | Zhao |
| 2012/0109148 A1 | 5/2012 | Bonner et al. |
| 2012/0116489 A1* | 5/2012 | Khairkhahan ......... A61N 1/375 607/127 |
| 2012/0150272 A1 | 6/2012 | Melsheimer |
| 2012/0172690 A1 | 7/2012 | Anderson et al. |
| 2012/0172691 A1 | 7/2012 | Greenberg et al. |
| 2012/0172891 A1 | 7/2012 | Lee |
| 2012/0172892 A1* | 7/2012 | Grubac ................ A61N 1/3756 606/129 |
| 2012/0172981 A1 | 7/2012 | DuMontelle |
| 2013/0035636 A1 | 2/2013 | Beasley et al. |
| 2013/0253309 A1 | 9/2013 | Allan et al. |
| 2013/0253342 A1 | 9/2013 | Griswold et al. |
| 2013/0253344 A1 | 9/2013 | Griswold et al. |
| 2013/0253346 A1 | 9/2013 | Griswold et al. |
| 2013/0268042 A1 | 10/2013 | Hastings et al. |
| 2014/0180306 A1* | 6/2014 | Grubac ................ A61N 1/3756 606/129 |
| 2014/0207149 A1 | 7/2014 | Hastings et al. |
| 2015/0045868 A1* | 2/2015 | Bonner ................ A61N 1/3756 607/126 |
| 2016/0243350 A9* | 8/2016 | Grubac ................ A61N 1/3756 |

FOREIGN PATENT DOCUMENTS

| | | |
|---|---|---|
| EP | 0571985 B1 | 12/1999 |
| EP | 1496956 B1 | 4/2011 |
| EP | 1812104 B1 | 11/2012 |
| EP | 1835962 B1 | 4/2015 |
| WO | 00059376 A1 | 10/2000 |
| WO | 00166151 A1 | 9/2001 |
| WO | 00230295 A1 | 4/2002 |
| WO | 003084398 A1 | 10/2003 |
| WO | 2004014456 A2 | 2/2004 |
| WO | 2005028023 A1 | 3/2005 |
| WO | 2006045073 A1 | 4/2006 |
| WO | 2007021340 A1 | 2/2007 |
| WO | 2007022180 A1 | 2/2007 |
| WO | 2009039400 | 3/2009 |
| WO | 2009120636 | 10/2009 |
| WO | 2009124287 A1 | 10/2009 |
| WO | 10088687 A1 | 5/2010 |

OTHER PUBLICATIONS

Luna Technologies, "About Distributed Sensing Technology" 2 pages (2010).
(PCT/US2011/066517) PCT Notification of Transmittal of the International Search Report and the Written Opinion of the International Searching Authority, dated Mar. 7, 2012, 8 pages.
(PCT/US2011/066540) PCT Notification of Transmittal of the International Search Report and the Written Opinion of the International Searching Authority, dated May 5, 2012, 10 pages.
Rozenman et al., "Wireless Acoustic Communication With a Miniature Pressure Sensor in the Pulmonary Artery Disease Surveillance and Therapy of Patients With Congestive Heart Failure", Journal of the American College of Cardiology, vol. 49, No. 7, 2007, 7 pages.
Notice of Allowance from U.S. Appl. No. 13/284,761, dated May 18, 2018, 8 pp.
Office Action from U.S. Appl. No. 15/809,518, dated Jan. 26, 2018, 15 pp.
Response to Office Action dated Jan. 26, 2018, from U.S. Appl. No. 15/809,518, filed Apr. 20, 2018, 12 pp.

* cited by examiner

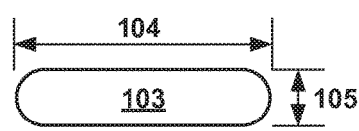
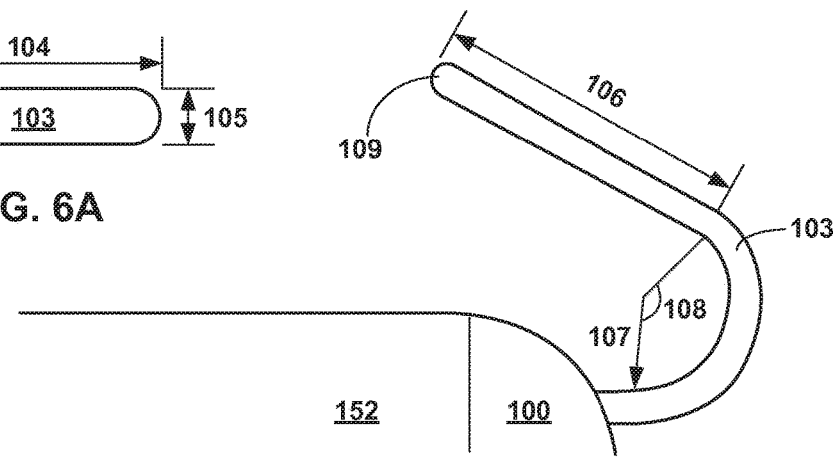
FIG. 6A
FIG. 6B
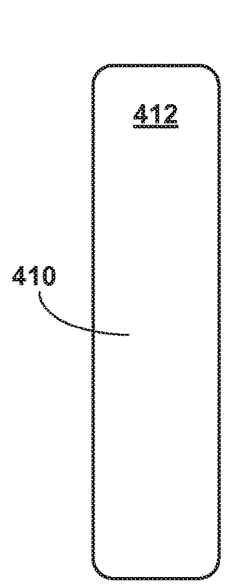
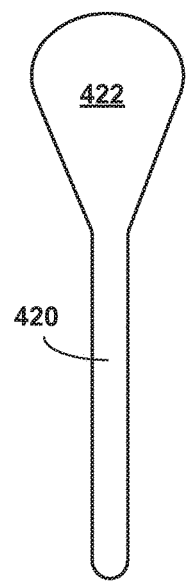
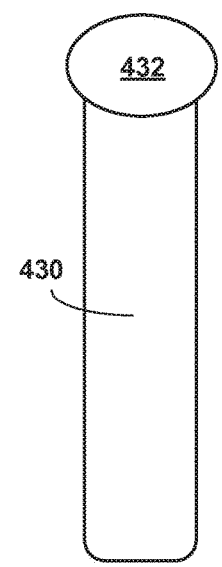
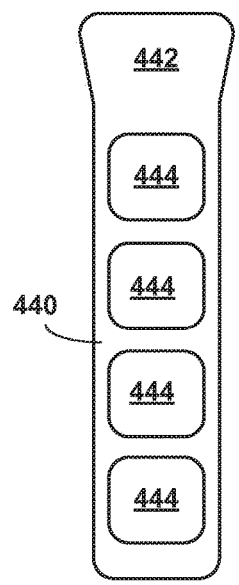
FIG. 7A    FIG. 7B    FIG. 7C    FIG. 7D

IMPLANTABLE MEDICAL DEVICE FIXATION

This application is a continuation of U.S. patent application Ser. No. 14/193,306, filed on Feb. 28, 2014, which is a continuation of U.S. patent application Ser. No. 13/096,881, filed on Apr. 28, 2011, now issued as U.S. Pat. No. 9,775,982, which claims the benefit of, and priority to, U.S. Provisional Application Ser. No. 61/428,067, filed on Dec. 29, 2010, the entire content of each of the applications identified above being incorporated by reference herein.

TECHNICAL FIELD

This disclosure relates to fixation techniques for implantable medical devices.

BACKGROUND

Medical devices such as electrical stimulators, leads, and electrodes are implanted to deliver therapy to one or more target sites within the body of a patient. To ensure reliable electrical contact between the electrodes and the target site, fixation of the device, lead, or electrodes is desirable.

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient. Medical devices with a housing configured for implantation within the patient may be referred to as implantable medical devices (IMDs).

Implantable cardiac pacemakers or cardioverter-defibrillators, for example, provide therapeutic electrical signals to the heart, e.g., via electrodes carried by one or more implantable medical leads. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an IMB may deliver pacing stimulation to the heart of the patient upon detecting tachycardia or bradycardia, and deliver cardioversion or defibrillation shocks to the heart upon detecting fibrillation.

Leadless IMDs may also be used to deliver therapy to a patient, and/or sense physiological parameters of a patient. In some examples, a leadless IMB may include one or more electrodes on its outer housing to deliver therapeutic electrical signals to patient, and/or sense intrinsic electrical signals of patient. For example, leadless cardiac devices, such as leadless pacemakers, may also be used to sense intrinsic depolarizations and/or other physiological parameters of the heart and/or deliver therapeutic electrical signals to the heart. A leadless cardiac device may include one or more electrodes on its outer housing to deliver therapeutic electrical signals and/or sense intrinsic depolarizations of the heart. Leadless cardiac devices may be positioned within or outside of the heart and, in some examples, may be anchored to a wall of the heart via a fixation mechanism.

SUMMARY

In general, this disclosure describes remotely-deployable active fixation tines for fixating IMDs or their components, such as leads, to patient tissues. As referred to herein an "IMD component," may be an entire IMB or an individual component thereof. Examples of IMDs that may be fixated to patient tissues with remotely-deployable active fixation tines according to this disclosure include leadless pacemakers and leadless sensing devices.

Active fixation tines disclosed herein may be deployed from the distal end of a catheter located at a desired implantation location for the IMD or its component. As further disclosed herein, active fixation tines provide a deployment energy sufficient to permeate a desired patient tissue and secure an IMD or its component to the patient tissue without tearing the patient tissue. This disclosure includes active fixation tines that allow for removal from a patient tissue followed by redeployment, e.g., to adjust the position of the IMD relative to the patient tissue. As different patient tissues have different physical and mechanical characteristics, the design of active fixation tines may be coordinated with patient tissue located at a selected fixation site within a patient. Multiple designs may be used to optimize fixation for a variety of patient tissues.

In one example, the disclosure is directed to an assembly comprising: an implantable medical device; and a set of active fixation tines attached to the implantable medical device. The active fixation tines in the set are deployable from a spring-loaded position in which distal ends of the active fixation tines point away from the implantable medical device to a hooked position in which the active fixation tines bend back towards the implantable medical device. The active fixation tines are configured to secure the implantable medical device to a patient tissue when deployed while the distal ends of the active fixation tines are positioned adjacent to the patient tissue.

In another example, the disclosure is directed to a kit for implanting an implantable medical device within a patient, the kit comprising: the implantable medical device; a set of active fixation tines attached to the implantable medical device. The active fixation tines in the set are deployable from a spring-loaded position in which distal ends of the active fixation tines point away from the implantable medical device to a hooked position in which the active fixation tines bend back towards the implantable medical device. The active fixation tines are configured to secure the implantable medical device to a patient tissue when deployed while the distal ends of the active fixation tines are positioned adjacent to the patient tissue. The kit further comprises a catheter forming a lumen sized to receive the implantable medical device and hold the active fixation tines in the spring-loaded position, wherein the lumen includes an aperture that is adjacent to the distal end of the catheter; and a deployment element configured to initiate deployment of the active fixation tines while the implantable medical device is positioned within the lumen of the catheter. Deployment of the active fixation tines while the implantable medical device is positioned within the lumen of the catheter causes the active fixation tines to pull the implantable medical device out of the lumen via the aperture that is adjacent to the distal end of the catheter.

In another example, the disclosure is directed to a method comprising: obtaining an assembly comprising an implantable medical device and a set of active fixation tines attached to the implantable medical device; positioning the distal ends of the active fixation tines adjacent to a patient tissue; and deploying the active fixation tines from a spring-loaded position in which distal ends of the active fixation tines point away from the implantable medical device to a hooked position in which the active fixation tines bend back towards the implantable medical device to secure the implantable medical device to the patient tissue.

The details of one or more aspects of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 6A-6B illustrate an active fixation tine showing measurements used to calculate performance characteristics of the active fixation tine.

FIGS. 7A-7D illustrate exemplary tine profiles.

DETAILED DESCRIPTION

Figure 1:
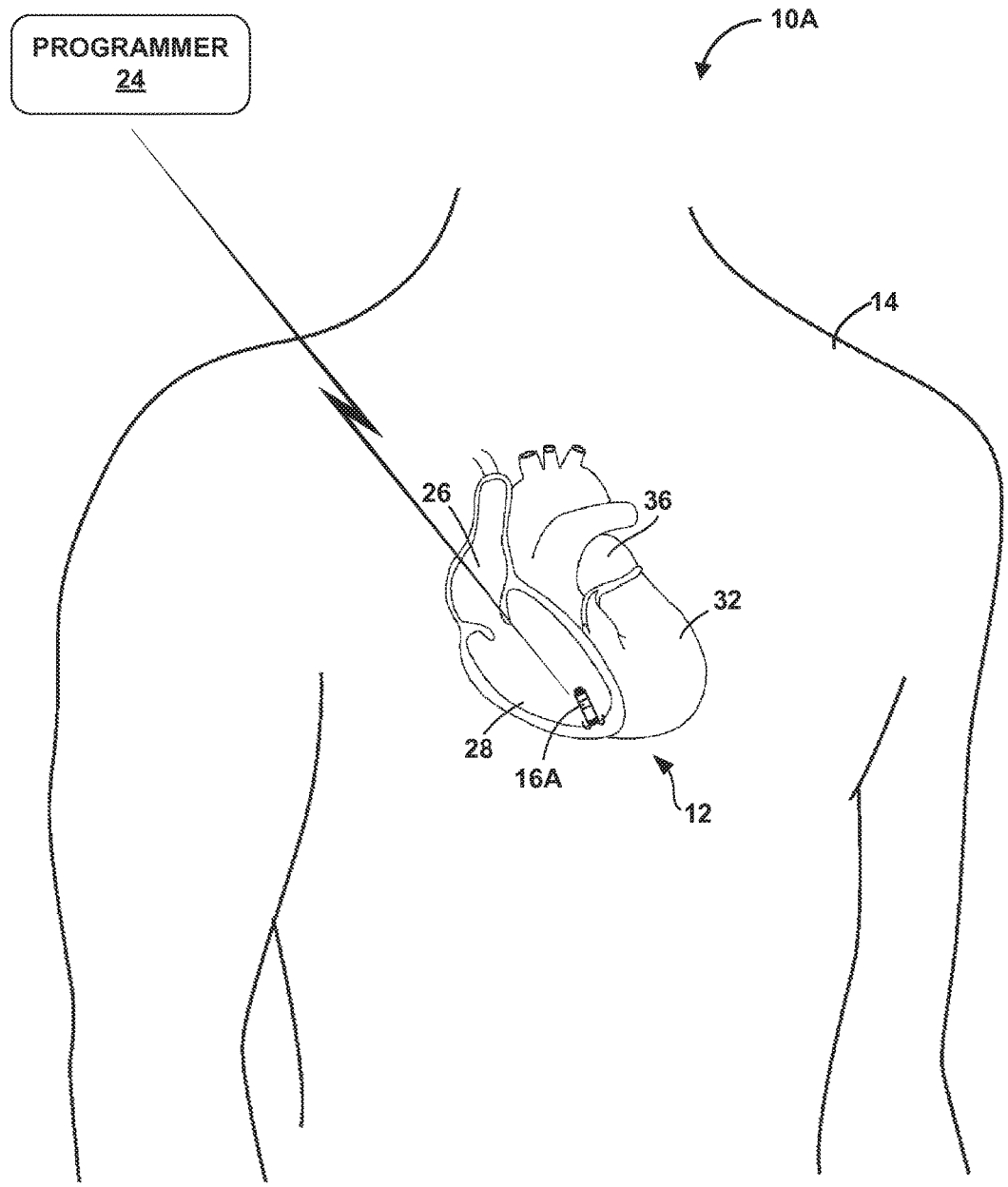
FIG. 1 is a conceptual diagram illustrating an example therapy system comprising a leadless IMB that may be used to monitor one or more physiological parameters of a patient and/or provide therapy to the heart of a patient.

Active fixation tines disclosed herein may be useful to secure an implantable medical device (IMD) including any components thereof, such as a medical lead, to a patient tissue during minimally invasive surgery. Minimally invasive surgery, such as percutaneous surgery, permits IMD implantation with less pain and recovery time than open surgery. However, minimally invasive surgery tends to be more complicated than open surgery. For example, forming device fixation requires a surgeon to manipulate instruments remotely, e.g., within the confines of an intravascular catheter. With techniques for remote deployment and fixation of IMDs it can be difficult to ensure adequate fixation while minimizing tissue damage. The active fixation tines disclosed are suitable for securing an IMD to a patient tissue. In addition, active fixation tines disclosed herein also allow for simple removal from a patient tissue without tearing the patient tissue followed by redeployment, e.g., to adjust the position of the IMD after first securing the IMD to the patient tissue.

In one example, active fixation tines disclosed herein may be deployed from the distal end of a catheter positioned by a clinician at a desired implantation location for the IMB. As further disclosed herein, active fixation tines provide a deployment energy sufficient to permeate a desired patient tissue and secure an IMD to the patient tissue without tearing the patient tissue. As different patient tissues have different physical and mechanical characteristics, the design of active fixation tines may be configured according to the properties of the patient tissue located at a selected fixation site within a patient. Multiple designs may be made for a variety of patient tissues, and available for selection based on the patient tissue at the fixation site.

Although various examples are described with respect to cardiac leads and leadless IMD, the disclosed active fixation tines may be useful for fixation of a variety of implantable medical devices in a variety of anatomical locations, and fixation of cardiac leads and leadless IMD is described for purposes of illustration. The described techniques can be readily applied securing catheters and other medical leads, e.g., for neurostimulation. As examples, medical leads with active fixation tines may be used for cardiac stimulation, gastric stimulation, functional electrical stimulation, peripheral nerve stimulation, spinal cord stimulation, pelvic nerve stimulation, deep brain stimulation, or subcutaneous neurological stimulation as well as other forms of stimulation. In addition, described techniques can be readily applied to IMDs including sensors, including leadless IMDs and IMDs with medical leads. As examples, IMDs including sensors and active fixation tines may include one or more of the following sensors: a pressure sensor, an electrocardiogram sensor, an oxygen sensor (for tissue oxygen or blood oxygen sensing), an accelerometer, a glucose sensor, a potassium sensor, a thermometer and/or other sensors.

FIG. 1 is a conceptual diagram illustrating an example therapy system 10A that may be used to monitor one or more physiological parameters of patient 14 and/or to provide therapy to heart 12 of patient 14. Therapy system 10A includes IMD 16A, which is coupled to programmer 24. IMD 16A may be an implantable leadless pacemaker that provides electrical signals to heart 12 via one or more electrodes (not shown in FIG. 1) on its outer housing. Additionally or alternatively, IMB 16A may sense electrical signals attendant to the depolarization and repolarization of heart 12 via electrodes on its outer housing. In some examples, IMB 16A provides pacing pulses to heart 12 based on the electrical signals sensed within heart 12.

IMD 16A includes a set of active fixation tines to secure IMB 16A to a patient tissue. In the example of FIG. 1, IMD 16A is positioned wholly within heart 12 proximate to an inner wall of right ventricle 28 to provide right ventricular (RV) pacing. Although IMD 16A is shown within heart 12 and proximate to an inner wall of right ventricle 28 in the example of FIG. 1, IMB 16A may be positioned at any other location outside or within heart 12. For example, IMD 16A may be positioned outside or within right atrium 26, left atrium 36, and/or left ventricle 32, e.g., to provide right atrial, left atrial, and left ventricular pacing, respectively.

Depending on the location of implant, IMD 16A may include other stimulation functionalities. For example, IMD 16A may provide atrioventricular nodal stimulation, fat pad stimulation, vagal stimulation, or other types of neurostimulation. In other examples, IMD 16A may be a monitor that senses one or more parameters of heart 12 and may not provide any stimulation functionality. In some examples, system 10A may include a plurality of leadless IMDs 16A, e.g., to provide stimulation and/or sensing at a variety of locations.

As discussed in greater detail with respect to FIGS. 3A-5H, IMD 16A includes a set of active fixation tines. The active fixation tines in the set are deployable from a spring-loaded position in which distal ends of the active fixation tines point away from the IMB to a hooked position in which the active fixation tines bend back towards the IMB. The active fixation tines allow IMD 16A to be removed from a patient tissue followed by redeployment, e.g., to adjust the position of IMB 16A relative to the patient tissue. For example, a clinician implanting IMD 16A may reposition IMD 16A during an implantation procedure if testing of IMD 16A indicates a poor electrode-tissue connection.

FIG. 1 further depicts programmer 24 in wireless communication with IMD 16A. In some examples, programmer 24 comprises a handheld computing device, computer workstation, or networked computing device. Programmer 24, shown and described in more detail below with respect to FIG. 9, includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16A. For example, the user may interact with programmer 24 to retrieve physiological or diagnostic information from IMB 16A. A user may also interact with programmer 24 to program IMD 16A, e.g., select values for operational parameters of the IMD 16A. For example, the user may use programmer 24 to retrieve information from IMD 16A regarding the rhythm of heart 12, trends therein over time, or arrhythmic episodes.

As an example, the user may use programmer 24 to retrieve information from IMB 16A regarding other sensed physiological parameters of patient 14 or information derived from sensed physiological parameters, such as intracardiac or intravascular pressure, activity, posture, tissue oxygen levels, blood oxygen levels, respiration, tissue perfusion, heart sounds, cardiac electrogram (EGM), intracardiac impedance, or thoracic impedance. In some examples, the user may use programmer 24 to retrieve information from IMD 16A regarding the performance or integrity of IMB 16A or other components of system 10A, or a power source of IMB 16A. As another example, the user may interact with programmer 24 to program, e.g., select parameters for, therapies provided by IMD 16A, such as pacing and, optionally, neurostimulation.

IMD 16A and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMB 16A implant site in order to improve the quality or security of communication between IMB 16A and programmer 24.

Figure 2:
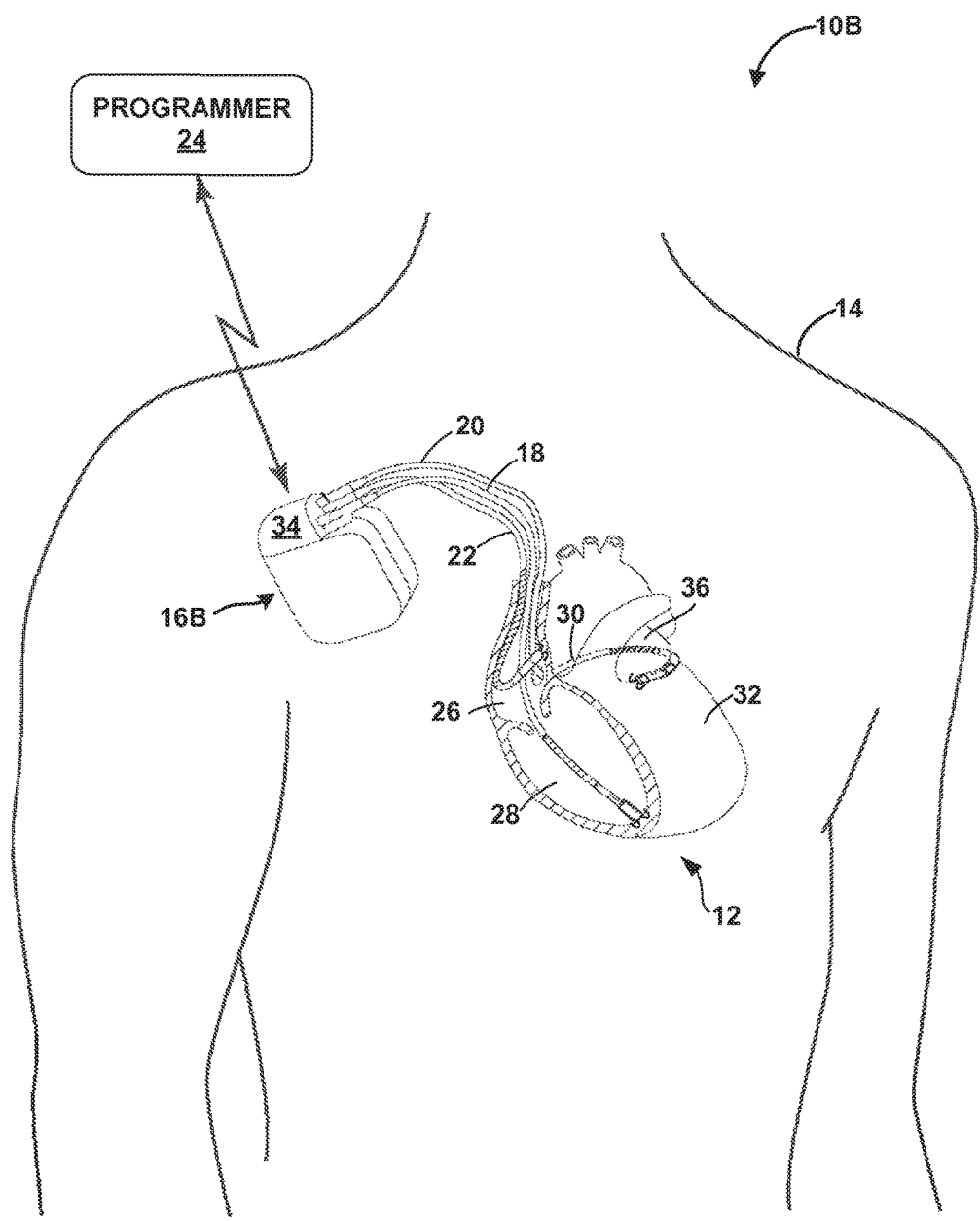
FIG. 2 is a conceptual diagram illustrating another example therapy system comprising an IMD coupled to a plurality of leads that may be used to monitor one or more physiological parameters of a patient and/or provide therapy to the heart of a patient.

FIG. 2 is a conceptual diagram illustrating another example therapy system 10B that may be used to monitor one or more physiological parameters of patient 14 and/or to provide therapy to heart 12 of patient 14. Therapy system 10B includes IMB 16B, which is coupled to medical leads 18, 20, and 22, and programmer 24. As referred to herein, each of IMD 16B and medical leads 18, 20 and 22 may be referred to generally as an IMB. In one example, IMD 16B may be an implantable pacemaker that provides electrical signals to heart 12 via electrodes coupled to one or more of leads 18, 20, and 22. IMD 16B is one example of an electrical stimulation generator, and is configured attached to the proximal end of medical leads 18, 20, and 22. In other examples, in addition to or alternatively to pacing therapy, IMD 16B may deliver neurostimulation signals. In some examples, IMD 16B may also include cardioversion and/or defibrillation functionalities. In other examples, IMD 16B may not provide any stimulation functionalities and, instead, may be a dedicated monitoring device. Patient 14 is ordinarily, but not necessarily, a human patient.

Medical leads 18, 20, 22 extend into the heart 12 of patient 14 to sense electrical activity of heart 12 and/or deliver electrical stimulation to heart 12. In the example shown in FIG. 2, right ventricular (RV) lead 18 extends through one or more veins (not shown), the superior vena cava (not shown), right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12. Right atrial (RA) lead 22 extends through one or more veins and the vena cava, and into the right atrium 26 of heart 12. RA lead 22 may be used to deliver RA pacing to heart 12.

In some examples, system 10B may additionally or alternatively include one or more leads or lead segments (not shown in FIG. 2) that deploy one or more electrodes within the vena cava or other vein, or within or near the aorta. Furthermore, in another example, system 10B may additionally or alternatively include one or more additional intravenous or extravascular leads or lead segments that deploy one or more electrodes epicardially, e.g., near an epicardial fat pad, or proximate to the vagus nerve. In other examples, system 10B need not include one of ventricular leads 18 and 20.

One or more of medical leads 18, 20, 22 may include a set of active fixation tines to secure a distal end of the medical lead to a patient tissue. The inclusion of active fixation tines for each medical leads 18, 20, 22 is merely exemplary. One or more of medical leads 18, 20, 22 could be secured by alternative techniques. For example, even though each of medical leads 18, 20 and 22 is shown with a set of active fixation tines to secure a distal end of the medical lead, LV lead 20, which extends through one or more veins and the vena cava and into the right atrium 26 of heart 12, may instead be fixed using passive fixation.

The active fixation tines in set active fixation tines attached to a medical lead are deployable from a spring-loaded position in which distal ends of the active fixation tines point away from the IMD to a hooked position in which the active fixation tines bend back towards the IMB. The active fixation tines allow the distal end of the medical lead be removed from a patient tissue followed by redeployment, e.g., to adjust the position of the distal end of the medical lead relative to the patient tissue. For example, a clinician implanting IMB 16B may reposition the distal end of a medical lead during an implantation procedure if testing of IMD 16B indicates a poor electrode-tissue connection.

IMD 16B may sense electrical signals attendant to the depolarization and repolarization of heart 12 via electrodes (described in further detail with respect to FIG. 4) coupled to at least one of the leads 18, 20, 22. In some examples, IMB 16B provides pacing pulses to heart 12 based on the electrical signals sensed within heart 12. The configurations of electrodes used by IMD 16B for sensing and pacing may be unipolar or bipolar.

IMD 16B may also provide neurostimulation therapy, defibrillation therapy and/or cardioversion therapy via electrodes located on at least one of the leads 18, 20, 22. For example, IMD 16B may deliver defibrillation therapy to heart 12 in the form of electrical pulses upon detecting ventricular fibrillation of ventricles 28 and 32. In some examples, IMD 16B may be programmed to deliver a progression of therapies, e.g., pulses with increasing energy levels, until a fibrillation of heart 12 is stopped. As another example, IMB 16B may deliver cardioversion or anti-tachycardia pacing (ATP) in response to detecting ventricular tachycardia, such as tachycardia of ventricles 28 and 32.

As described above with respect to IMB 16A of FIG. 1, programmer 24 may also be used to communicate with IMB 16B. In addition to the functions described with respect to IMD 16A of FIG. 1, a user may use programmer 24 to retrieve information from IMD 16B regarding the performance or integrity of leads 18, 20 and 22 and may interact with programmer 24 to program, e.g., select parameters for, any additional therapies provided by IMD 16B, such as cardioversion and/or defibrillation.

Leads 18, 20, 22 may be electrically coupled to a signal generator and a sensing module of IMB 16B via connector block 34. In some examples, proximal ends of leads 18, 20, 22 may include electrical contacts that electrically couple to respective electrical contacts within connector block 34 of IMD 16B. In some examples, a single connector, e.g., an IS-4 or DF-4 connector, may connect multiple electrical contacts to connector block 34. In addition, in some examples, leads 18, 20, 22 may be mechanically coupled to connector block 34 with the aid of set screws, connection pins, snap connectors, or another suitable mechanical coupling mechanism.

The configuration of system 10B illustrated in FIG. 2 is merely one example. In other examples, a system may include epicardial leads and/or patch electrodes instead of or in addition to the transvenous leads 18, 20, 22 illustrated in FIG. 2. Further, IMD 16B need not be implanted within patient 14. In examples in which IMB 16B is not implanted in patient 14, IMB 16B may deliver defibrillation pulses and other therapies to heart 12 via percutaneous leads that extend through the skin of patient 14 to a variety of positions within or outside of heart 12. For each of these examples, any number of the medical leads may include a set of active fixation tines on a distal end of the medical lead in accordance with the techniques described herein.

In addition, in other examples, a system may include any suitable number of leads coupled to IMB 16B, and each of the leads may extend to any location within or proximate to heart 12. For example, other examples of systems may include three transvenous leads located as illustrated in FIG. 2, and an additional lead located within or proximate to left atrium 36. Other examples of systems may include a single lead that extends from IMD 16B into right atrium 26 or right ventricle 28, or two leads that extend into a respective one of the right ventricle 28 and right atrium 26. Any electrodes located on these additional leads may be used in sensing and/or stimulation configurations. In each of these examples, any number of the medical leads may include a set of active fixation tines on a distal end of the medical lead in accordance with the techniques described herein.

Figure 3A:
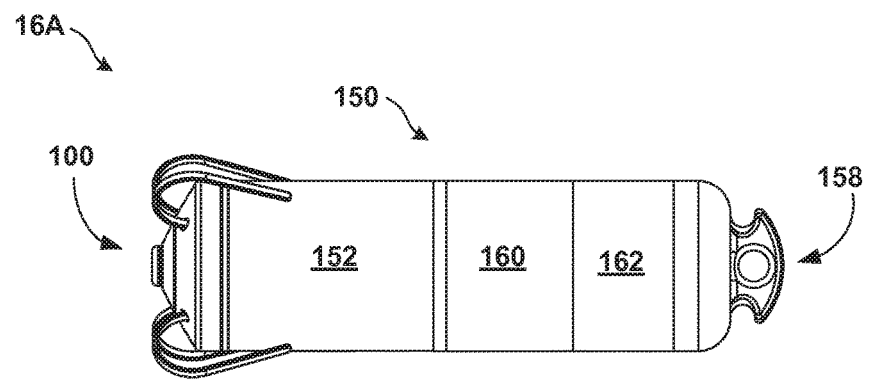
FIGS. 3A-3B illustrate the leadless IMD of FIG. 1 in further detail.
Figure 3B:
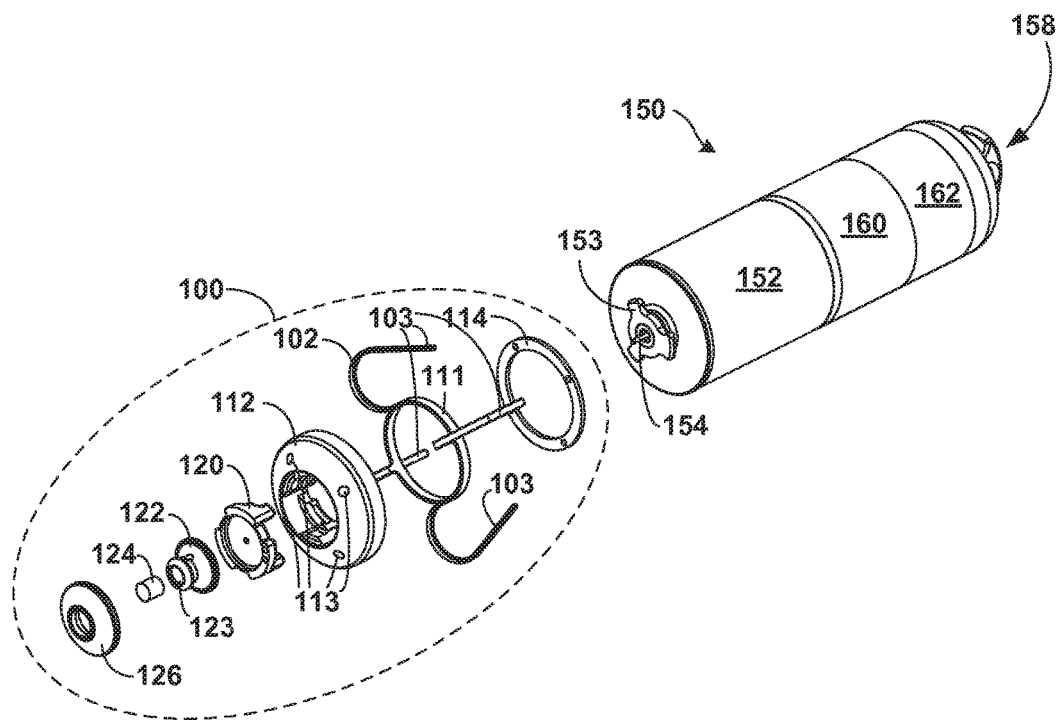

FIGS. 3A-3B illustrate leadless IMD 16A of FIG. 1 in further detail. In the example of FIGS. 3A and 3B, leadless IMD 16A includes tine fixation subassembly 100 and electronic subassembly 150. Tine fixation subassembly 100 is configured to anchor leadless IMD 16A to a patient tissue, such as a wall of heart 12.

Electronic subassembly 150 includes control electronics 152, which controls the sensing and/or therapy functions of IMD 16A, and battery 160, which powers control electronics 152. As one example, control electronics 152 may include sensing circuitry, a stimulation generator and a telemetry module. As one example, battery 160 may comprise features of the batteries disclosed in U.S. patent application Ser. No. 12/696,890, titled IMPLANTABLE MEDICAL DEVICE BATTERY and filed Jan. 29, 2010, the entire contents of which are incorporated by reference herein.

The housings of control electronics 152 and battery 160 are formed from a biocompatible material, such as a stainless steel or titanium alloy. In some examples, the housings of control electronics 152 and battery 160 may include an insulating coating. Examples of insulating coatings include parylene, urethane, PEEK, or polyimide among others. Electronic subassembly 150 further includes anode 162, which may include a low polarizing coating, such as titanium nitride, iridium oxide, ruthenium oxide among others. The entirety of the housings of control electronics 152 and battery 160 are electrically connected to one another, but only anode 162 is uninsulated. In other examples, the entirety of the housing of battery 160 or the entirety of the housing of electronic subassembly 150 may function as an anode instead of providing a localized anode such as anode 162. Alternatively, anode 162 may be electrically isolated from the other portions of the housings of control electronics 152 and battery 160.

Delivery tool interface 158 is located at the proximal end of electronic subassembly 150. Delivery tool interface 158 is configured to connect to a delivery device, such as catheter 200 (FIG. 5A) used to position IMD 16A during an implantation procedure. Tine fixation subassembly interface 153 and feedthrough pin 154 are located at the distal end of electronic subassembly 150. Tine fixation subassembly interface 153 includes three tabs that interlock with tine fixation subassembly 100.

As best illustrated in FIG. 3B, tine fixation subassembly 100 includes fixation element 102, header body 112, header cap 114, locking tab 120, electrode 122, monolithic controlled release device (MCRD) 124 and filler cap 126. Fixation element 102 includes a set of four active fixation tines 103 that are deployable from a spring-loaded position in which distal ends of active fixation tines 103 point away from electronic subassembly 150 to a hooked position in which active fixation tines 103 bend back towards electronic subassembly 150. For example, active fixation tines 103 are shown in the hooked position in FIG. 3A. As discussed in further detail with respect to FIGS. 4A-5H, active fixation tines 103 are configured to secure IMD 16A to a patient tissue, e.g., a tissue inside the heart or outside the heart, when deployed while the distal ends of active fixation tines 103 are positioned adjacent to the patient tissue. In different examples, active fixation tines 103 may be positioned adjacent to patient tissue such that distal ends 109 penetrate the patient tissue prior to deployment, positioned adjacent to patient tissue such that distal ends 109 contact but do not penetrate the patient tissue prior to deployment or positioned adjacent to patient tissue such that distal ends 109 are near to but do not contact or penetrate the patient tissue prior to deployment.

Fixation element 102 may be fabricated of a shape memory material, which allows active fixation tines 103 to bend elastically from the hooked position to the spring-loaded position. As an example, the shape memory material may be shape memory alloy such as Nitinol. In one example, fixation element 102 including active fixation tines 103 and base 111, may be manufactured by cutting fixation element 102 as a unitary component from a hollow tube of Nitinol, bending the cut tube to form the hooked position shape of active fixation tines 103 and heat-treating fixation element 102 while holding active fixation tines 103 in the hooked position. Sharp edges of fixation element 102 may be rounded off to improve fatigue loading and reduce tearing of patient tissue during deployment and retraction of active fixation tines 103.

In some examples, all or a portion of fixation element 102, such as active fixation tines 103, may include one or more coatings. For example, fixation element 102 may include a radiopaque coating to provide visibility during fluoroscopy. In one such example, fixation element 102 may include one or more radiopaque markers. As another example, fixation element 102 may be coated with a tissue growth promoter or a tissue growth inhibitor. A tissue growth promoter may be useful to increase the holding force of active fixation tines 103, whereas a tissue growth inhibitor may be useful to facilitate removal of IMB 16A during an explantation procedure, which may occur many years after the implantation of IMD 16A.

During assembly of IMB 16A, prior to being mounted to electronic subassembly 150, fixation element 102 may be mounted in a header including header body 112 and header cap 114. For example, fixation element 102 may be mounted such that one tine extends though each of holes 113 in header body 112. Then header cap 114 is positioned over base 111 of fixation element 102 and secured to header body 112. As an example, header body 112 and header cap 114 may be fabricated of a biocompatible polymer such as polyether ether ketone (PEEK). Header body 112 and header cap 114 may function to electrically isolate fixation element 102 from electronic subassembly 150 and feedthrough pin 154. In other examples, fixation element 102 itself may be used as an electrode for stimulation and/or sensing a physiological condition of a patient and may electrically connect to control electronics 152.

During assembly of IMB 16A, once fixation element 102 is assembled with header body 112 and header cap 114, fixation element 102, header body 112 and header cap 114 are mounted to the tabs of tine fixation subassembly interface 153 on electronic subassembly 150 by positioning header body 112 over the tabs of tine fixation subassembly interface 153 and rotating header body 112 to interlock header body 112 with the tabs of tine fixation subassembly interface 153. Feedthrough pin 154 extends through the center of header body 112 once header body 112 is secured to tine fixation subassembly interface 153.

During assembly of IMB 16A, after header body 112 is secured to tine fixation subassembly interface 153, locking tab 120 is positioned over feedthrough pin 154. As an example, locking tab 120 may be fabricated of a silicone material. Next, electrode 122 is positioned over locking tab 120 and feedthrough pin 154, and then mechanically and electrically connected to feedthrough pin 154, e.g., using a laser weld. As an example, electrode 122 may comprise a biocompatible metal, such as an iridium alloy or a platinum alloy.

MCRD 124 is located within recess 123 of electrode 122. In the illustrated example, MCRD 124 takes the form of a cylindrical plug. In other examples, an MCRD band may positioned around the outside of the electrode rather than configured as a cylindrical plug. MCRD 124 may be fabricated of a silicone based polymer, or other polymers. MCRD 124 may incorporate an anti-inflammatory drug, which may be, for example, the sodium salt of dexamethasone phosphate. Because MCRD 124 is retained within recess 123 of electrode 122, migration of the drug contained in MCRD 124 is limited to the tissue in contact with the distal end of electrode 122. Filler cap 126 is positioned over electrode 122. As an example, filler cap 126 may be fabricated of a silicone material and positioned over both electrode 122 and locking tab 120 during assembly of IMD 16A.

As different patient tissues have different physical and mechanical characteristics, active fixation tines 103 may be specifically designed to perform with patient tissues having specific characteristics. For example, active fixation tines 103 may be designed to provide a selected fixation force, designed to penetrate to a particular depth of a patient tissue, designed to penetrate to a particular layer of patient tissue (as different tissue layers may have different mechanical properties) and/or designed to facilitate removal and redeployment from the patient tissue without tearing the patient tissue, either on deployment or removal. Multiple designs of active fixation tine 103 may be used to optimize fixation for a variety of patient tissues. The design of active fixation tine 103 is discussed in further detail with respect to FIGS. 6A-6B. In addition, the specific design of tine fixation subassembly 100 is not germane to the operation of active fixation tines 103, and a variety of techniques may be used to attach a set of active fixation tines to an IMD.

Figure 4A:
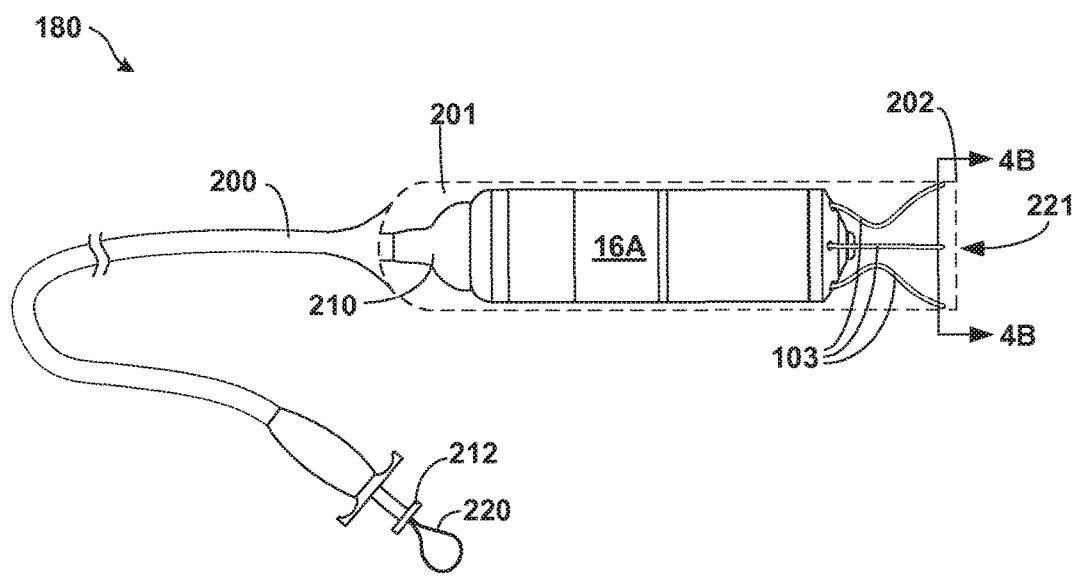
FIGS. 4A-4B illustrate an assembly including the leadless IMB of FIG. 1 and a catheter configured to deploy the leadless IMB of FIG. 1

FIG. 4A illustrates assembly 180, which includes leadless IMB 16A and catheter 200, which is configured to remotely deploy IMD 16A. Catheter 200 may be a steerable catheter or be configured to traverse a guidewire. In any case, catheter 200 may be directed within a body lumen, such as a vascular structure to a target site in order to facilitate remote positioning and deployment of IMB 16A. In particular, catheter 200 forms lumen 201, which is sized to receive IMD 16A at the distal end of catheter 200. For example, the inner diameter of lumen 201 at the distal end of catheter 200 may be about the same size as the outer diameter of IMD 16A. When IMD 16A is positioned within lumen 201 at the distal end of catheter 200, lumen 201 holds active fixation tines 103 in the spring-loaded position shown in FIG. 4A. In the spring-loaded position, active fixation tines 103 store enough potential energy to secure IMD 16A to a patient tissue upon deployment.

Lumen 201 includes aperture 221, which is positioned at the distal end of catheter 200. Aperture 221 facilitates deployment of IMD 16A. Deployment element 210 is positioned proximate to IMB 16A in lumen 201. Deployment element 210 configured to initiate deployment of active fixation tines 103. More particularly, a clinician may remotely deploy IMD 16A by pressing plunger 212, which is located at the proximal end of catheter 200. Plunger 212 connects directly to deployment element 210, e.g., with a wire or other stiff element running through catheter 200, such that pressing on plunger 212 moves deployment element 210 distally within lumen 201. As deployment element 210 moves distally within lumen 201, deployment element 210 pushes IMD 16A distally within lumen 201 and towards aperture 221. Once the distal ends 109 of active fixation tines 103 reach aperture 221, active fixation tines 103 pull IMD 16A out of lumen 201 via aperture 221 as active fixation tines 103 move from a spring-loaded position to a hooked position to deploy IMD 16A. The potential energy released by active fixation tines 103 is sufficient to penetrate a patient tissue and secure IMB 16A to the patient tissue.

Tether 220 is attached to delivery tool interface 158 (not shown in FIG. 4A) of IMB 16A and extends through catheter 200. Following deployment of IMB 16A, a clinician may remotely pull IMD 16A back into lumen 201 by pulling on tether 220 at the proximal end of catheter 200. Pulling IMD 16A back into lumen 201 returns active fixation tines 103 to the spring-loaded position from the hooked position. The proximal ends of active fixation tines 103 remain fixed to the housing of IMB 16A as active fixation tines 103 move from the spring-loaded position to the hooked position and vice-versa. Active fixation tines 103 are configured to facilitate releasing IMD 16A from patient tissue without tearing the tissue when IMB 16A is pulled back into lumen 201 by tether 220. A clinician may redeploy IMB 16A with deployment element 210 by operating plunger 212.

Figure 4B:
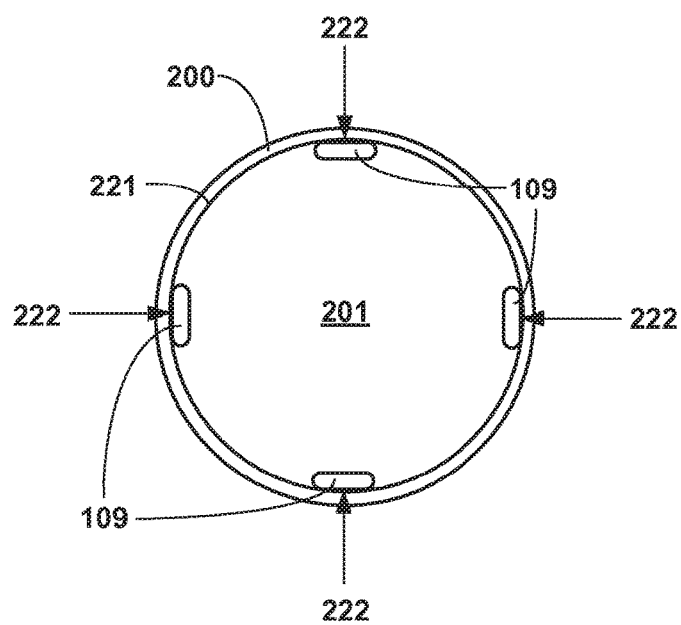

FIG. 4B is a sectional view of the distal end of assembly 180 in which IMD 16A is positioned within lumen 201. Lumen 201 holds active fixation tines 103 in a spring-loaded position. Distal ends 109 of active fixation tines 103 are indicated in FIG. 4B. As shown in FIG. 4B, the four active fixation tines 103 are positioned substantially equidistant from each other in a circular arrangement. As best seen in FIG. 3A, active fixation tines 103 are oriented outwardly relative to the circular arrangement.

Positioning active fixation tines 103 substantially equidistant from each other in a circular arrangement creates opposing radial forces 222 when active fixation tines 103 are deployed in unison. This allows the combined forces of active fixation tines 103 acting on the distal end of catheter 200 to pull IMD 16A about perpendicularly out of aperture 221. When the active fixation tines are deployed while aperture 221 and distal ends 109 of active fixation tines 103 are positioned adjacent to a patient tissue, the forces of active fixation tines 103 acting on the distal end of catheter 200 combine to pull IMD 16A straight out from aperture 221 and directly towards the patient tissue. While IMD 16A includes a set of four active fixation tines, a set of more or less than four active fixation tines may be used. For example, as few as two active fixation tines may provide opposing radial forces 222; however, a set of at least three active fixation tines may provide better directional consistency in the deployment of an IMB such as IMD 16A.

Distal ends 109 of active fixation tines 103 include substantially flat outer surfaces to register active fixation tines 103 on the inner surface of lumen 201. The flat outer surfaces of active fixation tines 103 help ensure that the interaction between active fixation tines 103 and the inner surface of lumen 201 during deployment of IMD 16A provides opposing radial forces 222.

FIGS. 5A-5H illustrate example techniques for securing IMB 16A to patient tissue 300 using catheter 200. As an example, patient tissue 300 may be a heart tissue, such as the inner wall of the right ventricle. For simplicity, a set of only two active fixation tines 103 are shown in each of FIGS. 5A-5H; however, the described techniques for securing IMD 16A to patient tissue 300 are equally applicable to IMDs including a set of more than two active fixation tines 103.

Figure 5A:
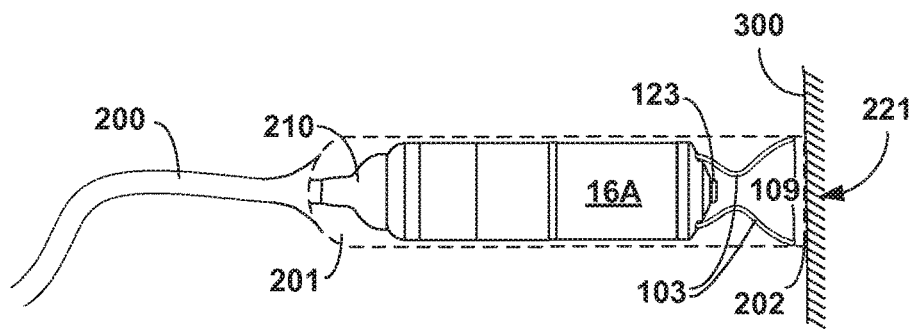
FIGS. 5A-5H illustrate techniques for securing the leadless IMB of FIG. 1 to a patient tissue using the catheter of FIG. 4A-4B.

FIG. 5A illustrates IMD 16A within lumen 201 of catheter 200. Lumen 201 holds active fixation tines 103 in a spring-loaded position in which distal ends 109 of active fixation tines 103 point away from IMD 16A. Aperture 221 is positioned adjacent patient tissue 300. The distal end 202 of catheter 200 may not pressed forcefully into patient tissue 300, as pressing patient tissue 300 would alter the mechanical characteristics of patient tissue 300. As active fixation tines 103 may be designed accordingly to the mechanical characteristics of patient tissue 300, altering the mechanical characteristics of patient tissue 300 may undesirably alter the interaction of active fixation tines 103 and patient tissue 300 during deployment of active fixation tines 103. In other examples, it may be desirable to alter the mechanical characteristics of patient tissue 300 for deployment, by significantly pressing on patient tissue 300 during deployment or by otherwise altering the mechanical characteristics of patient tissue 300, to achieve a desired interaction (e.g., tissue permeation, fixation depth, etc.) between patient tissue 300 and active fixation tines 103 during deployment of active fixation tines 103.

Figure 5B:
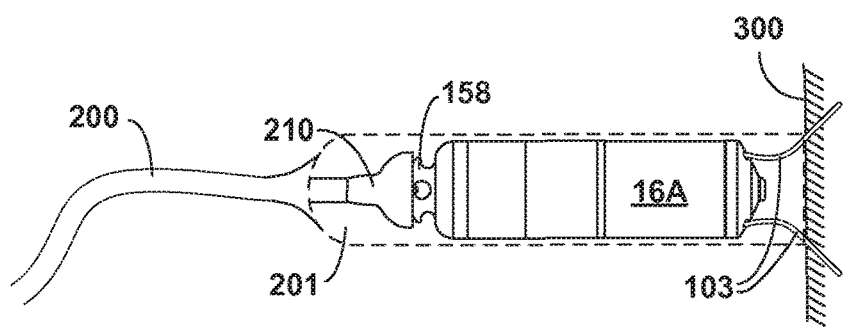
Figure 5C:
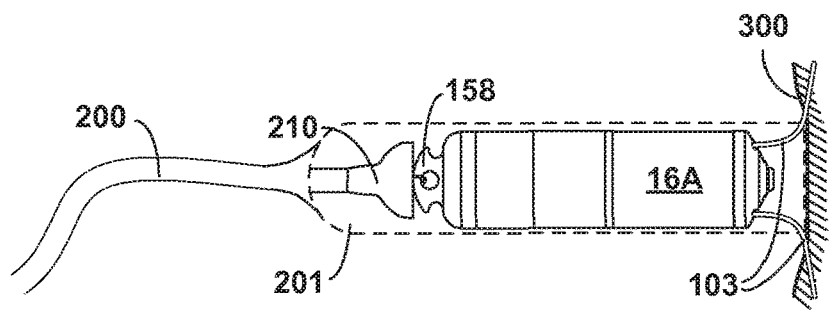

FIG. 5B illustrates IMD 16A shortly after a clinician remotely activated active fixation tines 103 using deployment element 210 by pressing on plunger 212 (FIG. 4A). As the clinician pressed plunger 212, deployment element 210 pushed IMD 16A distally within lumen 201. Once the distal ends 109 of active fixation tines 103 reached aperture 221, active fixation tines 103 began to pull IMD 16A out of lumen 201 via aperture 221. Distal ends 109 of active fixation tines 103 then penetrated patient tissue 300. FIG. 5B illustrates active fixation tines 103 in a position after distal ends 109 of active fixation tines 103 penetrated patient tissue 300 and shortly after beginning the transition from a spring-loaded position to a hooked position.

Figure 5D:
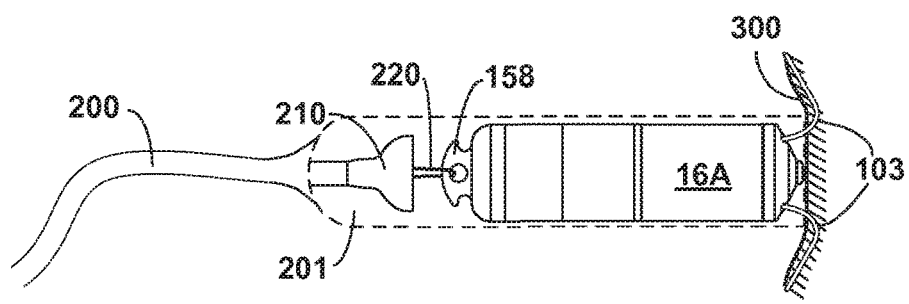
Figure 5E:
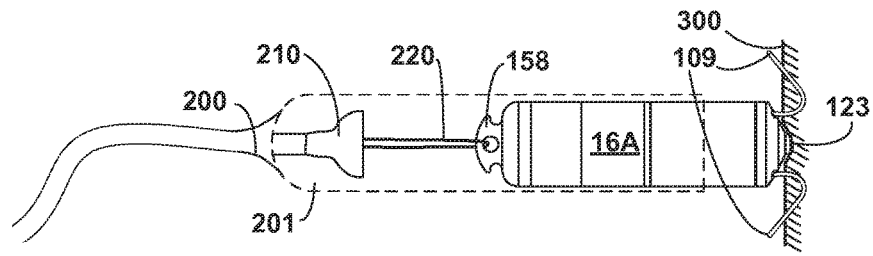
Figure 5F:
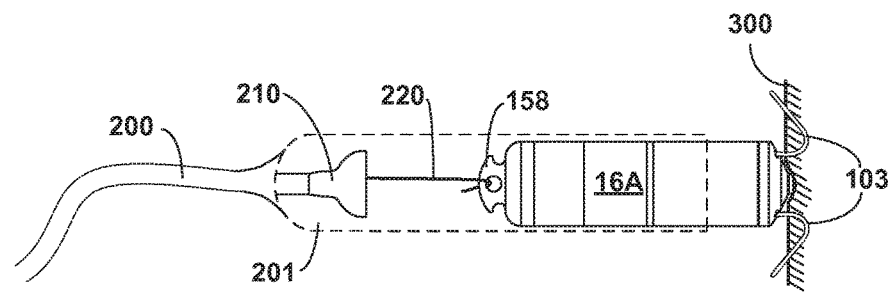

FIGS. 5B-5F illustrates active fixation tines 103 as they move from a spring-loaded position in which distal ends 109 of active fixation tines 103 point away from IMD 16A to a hooked position in which distal ends 109 of active fixation tines 103 bend back towards IMD 16A. FIGS. 5D-5F illustrate active fixation tines 103 in hooked positions. In FIG. 5D, distal ends 109 of active fixation tines 103 remain embedded in patient tissue 300, whereas FIGS. 5E-5F illustrate distal ends 109 of active fixation tines 103 penetrating out of patient tissue 300.

As active fixation tines 103 move from a spring-loaded position to a hooked position, potential energy stored in active fixation tines 103 is released as IMD 16A is pulled from lumen 201 via aperture 221. In addition, active fixation tines 103 penetrate patient tissue 300 to secure IMD 16A to patient tissue 300 such that electrode 123 (FIG. 5E) contacts patient tissue 300 within the center of the circular arrangement of active fixation tines 103. Active fixation tines 103 provide a forward pressure of electrode 123 onto tissue 300 to assure good electrode-tissue contact.

As active fixation tines 103 pull IMD 16A from lumen 201, tether 220, which is attached to delivery tool interface 158 of IMB 16A is exposed, e.g., as shown in FIG. 5E. Following deployment of IMB 16A, a clinician may remotely pull IMB 16A back into lumen 201 by pulling on tether 220 at the proximal end of catheter 200. For example, the clinician may perform a test of IMD 16A to evaluate a performance characteristic of electrode 123 while the IMB 16A is secured to patient tissue 300 as shown in FIG. 5E. If the test of IMD 16A indicates inadequate performance, the clinician may decide to redeploy IMB 16A. Pulling IMB 16A back into lumen 201 releases IMD 16A from patient tissue 300 and returns IMD 16A to the position shown in FIG. 5A. From this position a clinician may reposition IMD 16A as desired and redeploy IMB 16A.

Figure 5G:
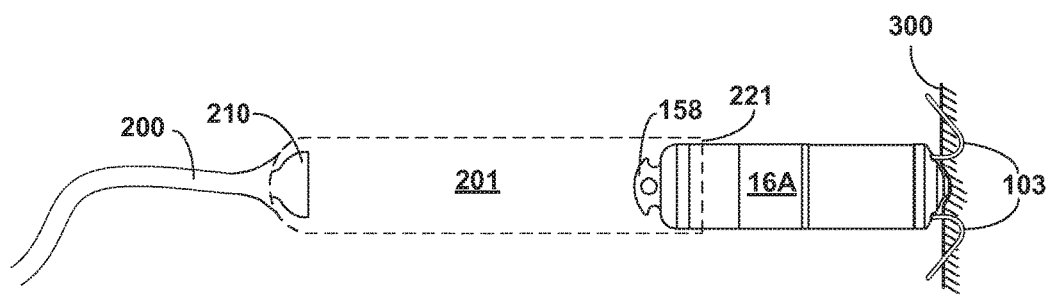
Figure 5H:
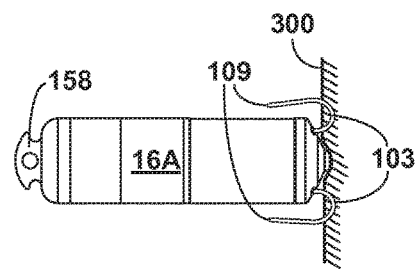

As shown in FIG. 5F, once IMD 16A is secured to patient tissue 300 in the desired position, the clinician may release IMD 16A from tether 220. For example, the clinician may sever tether 220 at the proximal end of catheter 200 and remove tether 220 from delivery tool interface 158 by pulling on one of the severed ends of tether 220. As shown in FIG. 5G, once IMD 16A is released from tether 220, the clinician may remove catheter 200, leaving IMD 16A secured to patient tissue 300. As shown in FIG. 5H, active fixation tines 103 may continue to migrate to a lower-potential energy hooked position over time. However, any of the hooked positions of active fixation tines 103 as shown in FIGS. 5D-5G may be sufficient to adequately secure IMD 16A to patient tissue 300.

While the techniques of FIGS. 5A-5H are illustrated with respect to IMD 16A, the techniques may also be applied to a different IMD, such as a medical lead including a set of active fixation tines like medical leads 18, 20, 22 of IMB 16B (FIG. 2). For example, such a medical lead may extend through a catheter during an implantation procedure. As such, deploying a medical lead may not require a separate deployment element within the catheter. Instead, simply pushing on the medical lead at the proximal end of the catheter may initiate deployment of a set of active fixation tines at the distal end of the medical lead by pushing the active fixation tines attached to the distal end of the medical lead out of the distal end of the catheter. Similarly retracting a medical lead for redeployment may not require a tether, but may instead simply involve pulling on the medical lead at the proximal end of the catheter.

FIGS. 6A-6B illustrate one active fixation tine 103 and further illustrate measurements used to calculate performance characteristics of active fixation tine 103. In particular, FIG. 6A illustrates a cross-section of active fixation tine 103 with width 104 and thickness (T) 105. FIG. 6B illustrates a side-view of active fixation tine 103 with tine length (L) 106, tine radius (r) 107 and tine angle 108.

The design of active fixation tine 103 is based on many criteria. As one example, an active fixation tine must penetrate a patient tissue when extended in the spring-loaded position. To meet this criteria, length 106 must be large enough to overcome the elasticity of the patient tissue such that distal end 109 of active fixation tine 103 permeates the patient tissue before active fixation tine 103 starts to bend significantly when deployed. For example, active fixation tine 103 will start to bend significantly when deployed once the curved portion of active fixation tine 103 reaches aperture 221 in distal end 202 of catheter 200 (FIG. 4A).

If distal end 109 of active fixation tine 103 were pointed, this would reduce the insertion force; however, adding a sharp point to active fixation tine 103 may cause tearing of patient tissue during deployment and removal of active fixation tine 103. For this reason, distal end 109 of active fixation tine 103 may be rounded. As one example, tine thickness 105 may be between about 0.005 inches and about 0.010 inches. In a further example, tine thickness 105 may be between about 0.006 inches and about 0.009 inches. In some examples, a tine may include a ball on its distal end to further resist tearing of patient tissue. One such example is shown in FIG. 7C.

As another example, the straight section providing length 106 of active fixation tine 103 must provide a column strength great enough to resist buckling from the force of the patient tissue before distal end 109 of active fixation tine 103 permeates the patient tissue. Column strength is dependent on length 106, width 104 and thickness 105, whereas the force required to permeate a patient tissue is dependent on mechanical properties of the tissue and the cross-sectional area of distal end 109 of active fixation tine 103. In addition, active fixation tine 103 may be designed to buckle before penetrating a particular tissue layer deeper than a targeted tissue layer. For example, when attaching to endocardial tissue, a tine may be designed to buckle before penetrating an epicardial layer of heart tissue to prevent penetrating an epicardial layer of heart tissue during deployment.

As another example, a set of active fixation tines may be designed to provide a selected holding force, which may also be referred to as the pull force required to remove a deployed set of active fixation tines from patient tissue (or other material). As one example, a holding force of between 1 and 5 newtons (N) or between 2 and 3 N may be suitable for securing IMD 16A within heart 12 (FIG. 1), while facilitating removal of the set of active fixation tines without tearing patient tissue.

Releasing an IMD from the tissue without tearing the tissue by pulling the implantable medical device away from the tissue includes, pulling on the implantable medical device to stretch the tissue until the tissue stiffness matches the tine straightening force, further pulling on the implantable medical device until the tines straighten without tearing the tissue, and continued pulling on the implantable medical device once the tines have straightened sufficiently to remove the tines from the patient tissue. The pulling distance required to release the tines from the tissue is longer than the length og the tines because of the elasticity of the tissue. For an example, in an example wherein the tines 7 mm long, removing the tines from the tissue may require pulling the IMD 12-20 mm away from the tissue.

Tine holding force may be considered the sum of tine straightening forces (to move the active fixation tines from the hooked position to the spring-loaded position) plus forces between the tine and the patient tissue, including frictional forces and forces that resist straightening of the tine in the patient tissue. Using finite element analysis, validated by actual testing, the following transfer function of the pull force required to remove a set of four active fixation tines deployed in cardiac tissue was determined, wherein $C_1$:$C_8$ each represents a constant greater than zero:

Pull Force=$-C_1+C_2*T-C_3*L+C_4*r-C_5*T*L-C_6*T*r-C_7*L*r+C_8*T*L*r$ (Equation 1)

A sensitivity analysis using a Pareto Chart of Effects on the importance of the different factors of Equation 1 indicated that pull force is most sensitive to tine thickness (59%), followed by tine radius (38%). Pull force showed the least sensitivity to tine length (3%). In addition, the interaction between thickness and radius was also important, whereas the other interactions were less significant.

In some examples, thickness greater than 0.009 inches or less than 0.003 inches may not be able to produce a pull forces suitable for securing IMD 16A within heart 12 (FIG. 1). Of course, in other examples, e.g., using a different selected holding forces, or assuming different material properties of active fixation tines 103 and/or of patient tissue tine thickness of greater than 0.009 inches or less than 0.003 inches may be suitable.

One additional design factor is fatigue loading, e.g., fatigue loading resulting from movement of a patient. For example, active fixation tines 103 may be designed to secure IMD 16A to patient heart 12 for a period of eighteen or more years. During that time, active fixation tines 103 may experience about 600 million heart beats from heart 12. In addition, sharp corners are detrimental to withstanding fatigue loading; for this reason, corners of active fixation tines 103 may be rounded, e.g., as best shown in FIG. 6A.

FIGS. 7A-7D illustrate exemplary profiles of the distal ends of different active fixation tine designs. In particular, FIG. 7A, illustrates rectangular profile 410 that provides a consistent width through its distal end 412. A tine providing rectangular profile 410 may also provide a generally consistent thickness. As an example, rectangular profile 410 is consistent with the profile of active fixation tines 103.

FIG. 7B illustrates profile 420, which includes an increased width at its distal end 422. A tine providing profile 420 may also provide a generally consistent thickness. Profile 420 may provide an increased insertion force and reduced column strength relative to tine profile 410. In addition, a tine providing profile 420 may reduce tearing of patient tissue during insertion and removal relative to a tine providing tine profile 410.

FIG. 7C illustrates profile 430, with includes an enlarged distal tip 432. Enlarged distal tip 432 is wider and thicker than the rest of a tine providing profile 430. A tine including enlarged distal tip 432 may reduce tearing of patient tissue during insertion and removal relative to a tine providing tine profile 410.

FIG. 7D illustrates profile 440, which includes an increased width at its distal end 442. A tine providing profile 440 may also provide a generally consistent thickness. Profile 440 also includes a series of apertures 444. After implantation, a tine including apertures 444 may provide a significant increase in holding strength relative to tine providing profile 410 as patient tissue grows around apertures 444. In addition, tine profile 440 may provide an increased insertion force and reduced column strength relative to tine profile 410.

Figure 8:
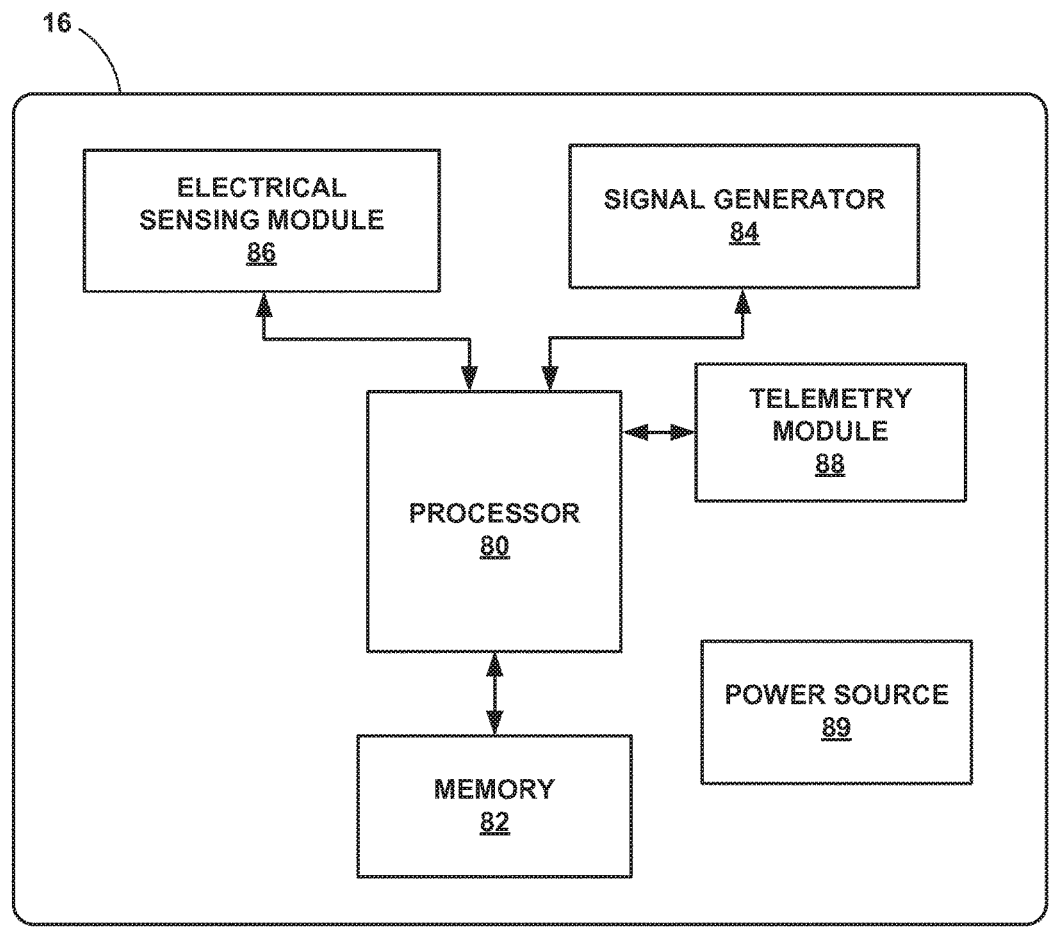
FIG. 8 is a functional block diagram illustrating an example configuration of an IMB.

FIG. 8 is a functional block diagram illustrating one example configuration of IMD 16A of FIGS. 1 and 3 or IMD 16B of FIG. 2 (referred to generally as IMD 16). In the example illustrated by FIG. 8, IMD 16 includes a processor 80, memory 82, signal generator 84, electrical sensing module 86, telemetry module 88, and power source 89. Memory 82 may include computer-readable instructions that, when executed by processor 80, cause IMD 16 and processor 80 to perform various functions attributed to IMD 16 and processor 80 herein. Memory 82 may be a computer-readable storage medium, including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof. Processor 80 controls signal generator 84 to deliver stimulation therapy to heart 12 according to operational parameters or programs, which may be stored in memory 82. For example, processor 80 may control signal generator 84 to deliver electrical pulses with the amplitudes, pulse widths, frequency, or electrode polarities specified by the selected one or more therapy programs.

Signal generator 84, as well as electrical sensing module 86, is electrically coupled to electrodes of IMD 16 and/or leads coupled to IMD 16. In the example illustrated in FIG. 8, signal generator 84 is configured to generate and deliver electrical stimulation therapy to heart 12. For example, signal generator 84 may deliver pacing, cardioversion, defibrillation, and/or neurostimulation therapy via at least a subset of the available electrodes. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver stimulation signals, e.g., pacing, cardioversion, defibrillation, and/or neurostimulation signals. The switch module may include a switch array, switch matrix, multiplexer, or any other type of switching device suitable to selectively couple a signal to selected electrodes.

Electrical sensing module 86 monitors signals from at least a subset of the available electrodes, e.g., to monitor electrical activity of heart 12. Electrical sensing module 86 may also include a switch module to select which of the available electrodes are used to sense the heart activity. In some examples, processor 80 may select the electrodes that function as sense electrodes, i.e., select the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chambers of heart 12, and may be configured to detect either R-waves or P-waves. In some examples, electrical sensing module 86 or processor 80 may include an analog-to-digital converter for digitizing the signal received from a sensing channel for electrogram (EGM) signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of the available electrodes appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by signal generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate. In some examples, a leadless IMD with a set of active fixation tines may include one or more sensors in addition to electrical sensing module 86. For example, a leadless IMD may include a pressure sensor and/or an oxygen sensor (for tissue oxygen or blood oxygen sensing).

Telemetry module 88 includes any suitable hardware, firmware, software or any combination thereof for communicating with another device, such as programmer 24 (FIGS. 1 and 2). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

In some examples, processor 80 may transmit an alert that a mechanical sensing channel has been activated to identify cardiac contractions to programmer 24 or another computing device via telemetry module 88 in response to a detected failure of an electrical sensing channel. The alert may include an indication of the type of failure and/or confirmation that the mechanical sensing channel is detecting cardiac contractions. The alert may include a visual indication on a user interface of programmer 24. Additionally or alternatively, the alert may include vibration and/or audible notification. Processor 80 may also transmit data associated with the detected failure of the electrical sensing channel, e.g., the time that the failure occurred, impedance data, and/or the inappropriate signal indicative of the detected failure.

Figure 9:
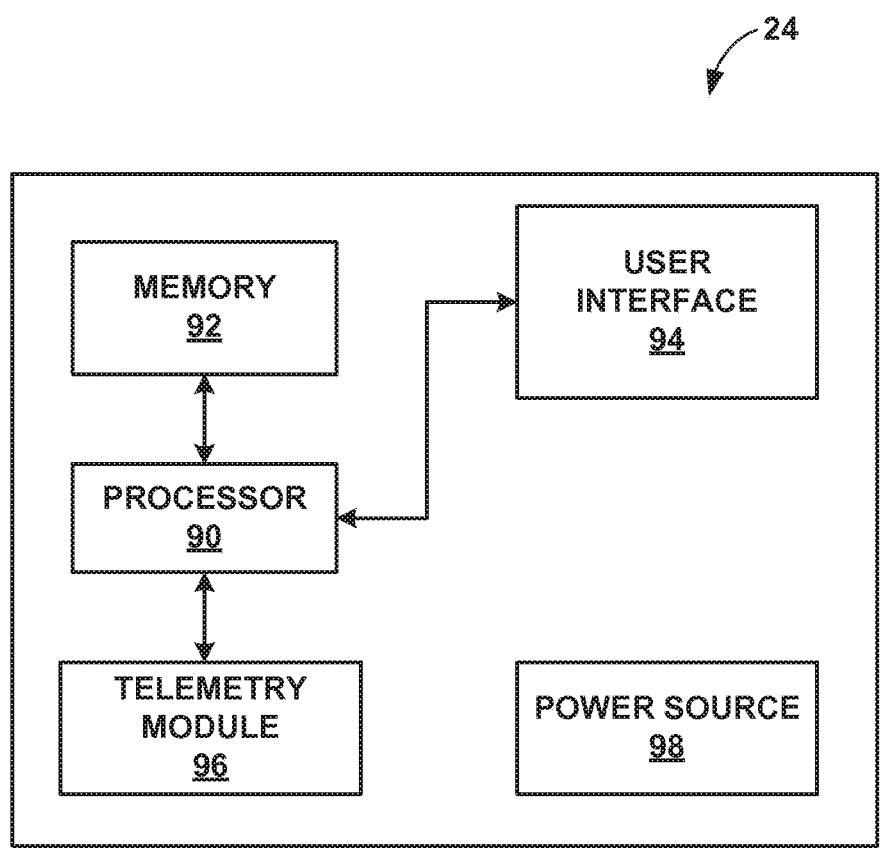
FIG. 9 is a block diagram of an example external programmer that facilitates user communication with an IMB.

FIG. 9 is a functional block diagram of an example configuration of programmer 24. As shown in FIG. 9, programmer 24 includes processor 90, memory 92, user interface 94, telemetry module 96, and power source 98. Programmer 24 may be a dedicated hardware device with dedicated software for programming of IMB 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, or modify therapy programs for IMB 16. The clinician may interact with programmer 24 via user interface 94, which may include a display to present a graphical user interface to a user, and a keypad or another mechanism for receiving input from a user.

Processor 90 can take the form of one or more microprocessors, DSPs, ASICs, FPGAs, programmable logic circuitry, or the like, and the functions attributed to processor 90 in this disclosure may be embodied as hardware, firmware, software or any combination thereof. Memory 92 may store instructions and information that cause processor 90 to provide the functionality ascribed to programmer 24 in this disclosure. Memory 92 may include any fixed or removable magnetic, optical, or electrical media, such as RAM, ROM, CD-ROM, hard or floppy magnetic disks, EEPROM, or the like. Memory 92 may also include a removable memory portion that may be used to provide memory updates or increases in memory capacities. A removable memory may also allow patient data to be easily transferred to another computing device, or to be removed before programmer 24 is used to program therapy for another patient. Memory 92 may also store information that controls therapy delivery by IMB 16, such as stimulation parameter values.

Programmer 24 may communicate wirelessly with IMD 16, such as using RF communication or proximal inductive interaction. This wireless communication is possible through the use of telemetry module 96, which may be coupled to an internal antenna or an external antenna. An external antenna that is coupled to programmer 24 may correspond to the programming head that may be placed over heart 12, as described above with reference to FIG. 1. Telemetry module 96 may be similar to telemetry module 88 of IMD 16 (FIG. 8).

Telemetry module 96 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth® specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 90 of programmer 24 and/or one or more processors of one or more networked computers may perform all or a portion of the techniques described in this disclosure with respect to processor 80 and IMD 16. For example, processor 90 or another processor may receive one or more signals from electrical sensing module 86, or information regarding sensed parameters from IMD 16 via telemetry module 96. In some examples, processor 90 may process or analyze sensed signals, as described in this disclosure with respect to IMD 16 and processor 80.

Figure 10:
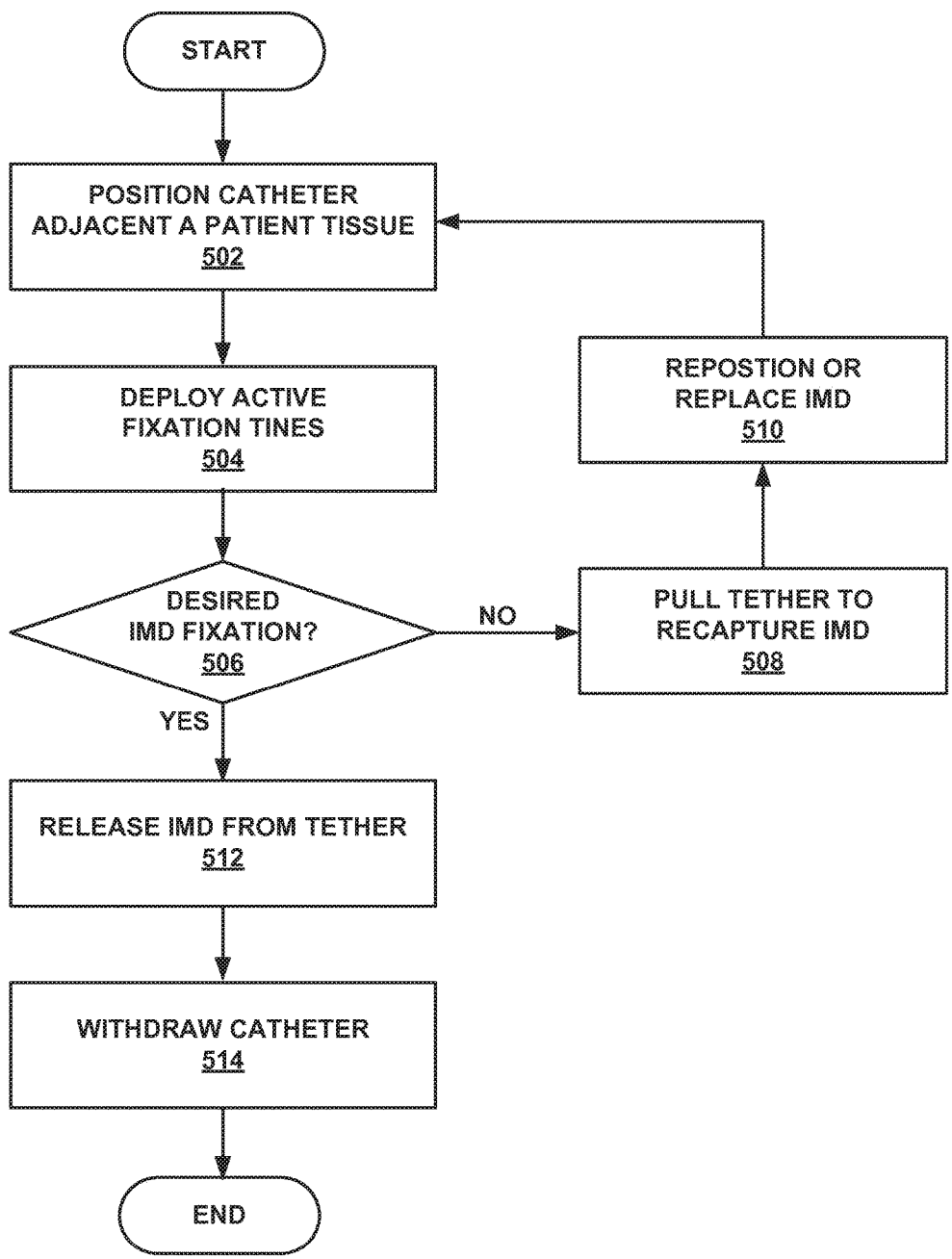
FIG. 10 is a flowchart illustrating techniques for implanting an implantable medical device within a patient.

FIG. 10 is a flowchart illustrating techniques for implanting an implantable medical device within a patient. The techniques of FIG. 10 are described with respect to IMD 16A, but are also applicable to other IMDs, such as deployment of leads associated with IMD 16B. First, assembly 180, which includes leadless IMD 16A and catheter 200, is positioned to a location within the patient, such as right ventricle 28 or a vasculature of the patient (502). Next, IMD 16A is deployed from catheter 200 to the location within the patient, such as right ventricle 28 or a vasculature of the patient (504). For example, the clinician may push on plunger 212 to deploy IMD 16A.

The clinician evaluates whether IMD 16A is adequately fixated and positioned within the patient (506). For example, the clinician may use fluoroscopy to evaluate whether IMD 16A is adequately fixated and positioned within the patient. If the clinician determines IMB 16A is inadequately positioned within the patient, the clinician operates catheter 200 to recapture IMD 16A by pulling on tether 220 (508). Then, the clinician either repositions distal end of catheter 200 or replaces IMB 16A with another IMD better suited for the implantation location (510). Then step 502 (see above) is repeated.

Once the clinician determines IMD 16A is adequately fixated within the patient (506), the clinician operates catheter 200 to fully release IMD 16A within the patient, e.g., by cutting tether 220 (512). Then, the clinician withdraws catheter 200, leaving IMD 16A secured within the patient (514).

Various examples of the disclosure have been described. These and other examples are within the scope of the following claims.

The invention claimed is:

1. An assembly comprising:
an implantable medical device comprising:
a plurality of electrodes; and
circuitry configured to deliver cardiac pacing stimulation via the plurality of electrodes; and
a set of fixation tines that are each deployable from a spring-loaded position to a hooked position, wherein each fixation tine of the set of fixations tines comprises a proximal end that is fixedly attached to a distal end of the implantable medical device in both the spring-loaded position and the hooked position, wherein each fixation tine of the set of fixations tines comprises a super-elastic material and is configured to have a column strength sufficient that a distal end of the tine penetrates cardiac tissue during deployment.

2. The assembly of claim 1, wherein a portion of each fixation tine adjacent the proximal end extends distally from the distal end of the implantable medical device in both the spring-loaded position and the hooked position.

3. The assembly of claim 1, wherein each fixation tine of the set of fixation tines is configured to be deployed from the spring-loaded position to the hooked position by releasing the fixation tine from the spring-loaded position and allowing the fixation tine to assume the hooked position.

4. The assembly of claim 1, wherein the set of fixation tines is configured to generate a deployment force during deployment that pulls the attached implantable medical device toward the cardiac tissue when the distal ends penetrate the cardiac tissue.

5. The assembly of claim 1, wherein each fixation tine of the set of fixation tines is positioned substantially equidistant from each other in a circular arrangement, wherein one of the electrodes is located at the distal end of the implantable medical device and generally centered within the circular arrangement.

6. The assembly of claim 5, wherein the set of fixation tines extend from the implantable medical device at a longitudinal position that is proximal to the electrode generally centered within the circular arrangement.

7. The assembly of claim 6, wherein each fixation tine of the set of fixation tines comprises a generally straight segment and an arcuate segment proximal to the generally straight segment, wherein, in the hooked position, a longitudinal position of a distal end of the generally straight segment is proximal the electrode, and a longitudinal position of at least a portion of the arcuate segment is distal the electrode.

8. The assembly of claim 1, wherein each fixation tine of the set of fixation tines comprises a generally straight segment and an arcuate segment proximal to the generally straight segment.

9. The assembly of claim 8, wherein the set of fixation tines are configured to generate a deployment force during deployment that pulls the attached implantable medical device toward the cardiac tissue, wherein each of the generally straight segments is configured to apply the deployment force to the cardiac tissue during the deployment.

10. The assembly of claim 9, wherein each of the generally straight segments is configured to have the column strength sufficient to penetrate the cardiac tissue.

11. The assembly of claim 10, wherein the cardiac tissue comprises endocardial tissue, the column strength insufficient to penetrate epicardial tissue.

12. The assembly of claim 1, wherein each fixation tine of the set of fixation tines defines a rectangular profile, and the distal end of each fixation tine of the set of fixation tines is rounded.

13. The assembly of claim 1, wherein the implantable medical device defines a longitudinal axis, wherein each fixation tine of the set of fixation tines includes at least a first portion that extends from the implantable medical device and a second portion that extends from the first portion, wherein in the spring-loaded position the first portion extends distally beyond the distal end of the implantable medical device and toward the longitudinal axis and the second portion extends distally from the first portion and away from the longitudinal axis, and wherein in the hooked position the first portion extends distally from the distal end of the implantable medical device the second portion bends back towards the implantable medical device.

14. The assembly of claim 13, wherein the second portion and the first portion define an arcuate shape in the spring-loaded position.

15. The assembly of claim 13, wherein the second portion is configured to bend back towards the implantable medical device such that at least some of the second portion is proximal to at least some of the first portion when the respective tine is in the hooked position.

16. The assembly of claim 1, further comprising a fixation element formed as a unitary component from a piece of the super-elastic material, the fixation element comprising a base and the set of fixation tines extending from the base.

17. The assembly of claim 1, wherein the implantable medical device is a leadless pacemaker.

18. An assembly comprising:
an implantable medical device comprising:
a plurality of electrodes; and
circuitry configured to deliver cardiac pacing stimulation via the plurality of electrodes; and
a set of fixation tines that are each deployable from a spring-loaded position to a hooked position, wherein each fixation tine of the set of fixations tines comprises a proximal end that is fixedly attached to a distal end of the implantable medical device in both the spring-loaded position and the hooked position,
wherein each fixation tine of the set of fixation tines is positioned substantially equidistant from each other in a circular arrangement, wherein one of the electrodes is located at the distal end of the implantable medical device and is generally centered within the circular arrangement, wherein each fixation tine of the set of fixation tines extends from the implantable medical device at a longitudinal position that is proximal to the electrode, and
wherein each fixation tine of the set of fixations tines comprises a super-elastic material and defines an oblong cross-section and is configured to have a column strength sufficient that a distal end of the tine penetrates cardiac tissue during deployment.

19. The assembly of claim 18, wherein a portion of the fixation tine adjacent the proximal end extends distally from the distal end of the implantable medical device in both the spring-loaded position and the hooked position.

20. The assembly of claim 18, wherein each fixation tine of the set of fixation tines is configured to be deployable by releasing the fixation tine from the spring-loaded position and allowing the fixation tine to assume the hooked position, wherein each fixation tine of the set of fixation tines is configured to generate a deployment force during deployment that pulls the attached implantable medical device toward the cardiac tissue when the distal ends penetrate the cardiac tissue.

21. The assembly of claim 18, wherein each fixation tine of the set of fixation tines comprises a generally straight segment configured to penetrate the cardiac tissue and an arcuate segment proximal to the generally straight segment, wherein each of the generally straight segments is configured to apply a deployment force to the cardiac tissue during the deployment.

22. The assembly of claim 18, wherein the implantable medical device defines a longitudinal axis, wherein each fixation tine of the set of fixation tines includes at least a first portion that extends from the implantable medical device and a second portion that extends from the first portion, wherein in the spring-loaded position the first portion extends distally beyond the distal end of the implantable medical device and toward the longitudinal axis and the second portion extends distally from the first portion and away from the longitudinal axis, and wherein in the hooked position the first portion extends distally from the distal end of the implantable medical device and the second portion bends back towards the implantable medical device.

23. A kit comprising:
an implantable medical device comprising:
 a plurality of electrodes;
 circuitry configured to deliver cardiac pacing stimulation via the plurality of electrodes; and
 a set of fixation tines that are each deployable from a spring-loaded position to a hooked position, wherein each fixation tine of the set of fixations tines comprises a proximal end that is fixedly attached to a distal end of the implantable medical device in both the spring-loaded position and the hooked position, wherein each fixation tine of the set of fixations tines comprises a super-elastic material and is configured to have a column strength sufficient that a distal end of the tine penetrates cardiac tissue during deployment; and
a catheter forming a lumen sized to receive the implantable medical device and hold each fixation tine of the set of fixation tines in the spring-loaded position, wherein each fixation tine of the set of fixation tines is configured to be deployed from the spring-loaded position to the hooked position by releasing the fixation tine from the spring-loaded position and allowing the fixation tine to assume the hooked position, wherein the catheter includes an aperture to the lumen that is adjacent to the distal end of the catheter.

24. The kit of claim 23, wherein a portion of the fixation tine adjacent the proximal end extends distally from the distal end of the implantable medical device in both the spring-loaded position and the hooked position.

25. The kit of claim 23, wherein each fixation tine of the set of fixation tines is configured to be deployed by pushing the implantable medical device towards the distal end of the catheter until the distal end of the fixation tine extends out of the aperture.

26. The kit of claim 25, wherein each fixation tine of the set of fixation tines is configured to generate a deployment force during deployment that pulls the attached implantable medical device at least partially out of the lumen via the aperture when distal ends of the set of fixation tines penetrate the cardiac tissue.

27. The kit of claim 23, wherein:
each fixation tine of the set of fixation tines is positioned substantially equidistant from each other in a circular arrangement;
one electrode of the plurality of electrodes is located at the distal end of the implantable medical device and is generally centered within the circular arrangement;
each fixation tine of the set of fixation tines extends from the implantable medical device at a longitudinal position that is proximal to the electrode;
each fixation tine of the set of fixation tines comprises a generally straight segment and an arcuate segment proximal to the generally straight segment; and
in the hooked position, a longitudinal position of a distal end of the generally straight segment is proximal the one electrode, and a longitudinal position of at least a portion of the arcuate segment is distal the one electrode.

28. The kit of claim 23, wherein:
each fixation tine of the set of fixation tines comprises a generally straight segment and an arcuate segment proximal to the generally straight segment;
each fixation tine of the set of fixation tines is configured to generate a deployment force during deployment that pulls the attached implantable medical device toward the cardiac tissue; and
each of the generally straight segments is configured to apply the deployment force to the cardiac tissue during the deployment.

29. The kit of claim 23, wherein the set of fixation tines are configured to generate a deployment force during deployment, wherein each tine of the set of fixation tines includes a relatively flattened section to register the tine on an inner surface of the catheter when generating the deployment force.

* * * * *